US009968291B2

(12) United States Patent
Hayes-Gill et al.

(10) Patent No.: US 9,968,291 B2
(45) Date of Patent: May 15, 2018

(54) MONITORING UTERINE ACTIVITY

(75) Inventors: Barrie Robert Hayes-Gill, Nottingham (GB); Jean-Francois Pieri, Nottingham (GB)

(73) Assignee: MONICA HEALTHCARE LIMITED, Nottingham (GB)

( * ) Notice: Subject to any disclaimer, the term of this patent is extended or adjusted under 35 U.S.C. 154(b) by 0 days. days.

(21) Appl. No.: 13/382,273

(22) PCT Filed: Jul. 6, 2010

(86) PCT No.: PCT/GB2010/001294
§ 371 (c)(1),
(2), (4) Date: Mar. 2, 2012

(87) PCT Pub. No.: WO2011/004147
PCT Pub. Date: Jan. 13, 2011

(65) Prior Publication Data
US 2012/0150010 A1 Jun. 14, 2012

(30) Foreign Application Priority Data
Jul. 6, 2009 (GB) .................................. 0911685.6

(51) Int. Cl.
*A61B 5/103* (2006.01)
*A61B 5/117* (2016.01)
(Continued)

(52) U.S. Cl.
CPC ........ *A61B 5/4356* (2013.01); *A61B 5/02411* (2013.01); *A61B 5/04882* (2013.01);
(Continued)

(58) Field of Classification Search
CPC ....................................................... A61B 5/00
(Continued)

(56) References Cited

U.S. PATENT DOCUMENTS 3,599,628 A * 8/1971 Abbenante et al. .......... 600/511
4,513,295 A 4/1985 Jones et al.
(Continued)

FOREIGN PATENT DOCUMENTS

| EP | 1220640 B1 | 5/2008 |
| EP | 1680018 B1 | 11/2008 |

(Continued)

OTHER PUBLICATIONS

Shono et al., "Fetal heart rate recorder for long-duration use in active full-term pregnant women", Jnl of Obstetrics and Gynecology, 1994 83, 2.
(Continued)

*Primary Examiner* — May Abouelela
(74) *Attorney, Agent, or Firm* — Perkins IP Law Group LLC; Jefferson Perkins

(57) ABSTRACT

An apparatus and method for detecting uterine activity uses cutaneous electrodes on the maternal abdomen to obtain electrophysiological signals that can be used to obtain fetal and maternal heart rate. The apparatus includes a first input for receiving electrical signals from the cutaneous electrodes and a second input for receiving movement signals indicative of a movement of the maternal body from a movement detector. A signal processor separates a uterine electromyogram signal from fetal and maternal heart rate signals and filters out motion artifacts from the electromyogram using the movement signals. An output presents electrohysterogram (EHG) data from the uterine electromyogram signal.

25 Claims, 14 Drawing Sheets

(51) Int. Cl.
*A61B 5/00* (2006.01)
*A61B 5/024* (2006.01)
*A61B 5/0488* (2006.01)
*A61B 5/11* (2006.01)

(52) U.S. Cl.
CPC .......... *A61B 5/4343* (2013.01); *A61B 5/4362* (2013.01); *A61B 5/721* (2013.01); *A61B 5/11* (2013.01)

(58) Field of Classification Search
USPC ....... 600/372, 382, 587, 591, 547, 300, 301, 600/595; 606/119
See application file for complete search history.

(56) References Cited

U.S. PATENT DOCUMENTS

| | | | | |
|---|---|---|---|---|
| 4,781,200 | A * | 11/1988 | Baker | 600/483 |
| 4,966,161 | A * | 10/1990 | Wallace et al. | 600/561 |
| 4,989,615 | A * | 2/1991 | Hochberg | 600/587 |
| 5,042,499 | A * | 8/1991 | Frank et al. | 600/511 |
| 5,197,472 | A * | 3/1993 | DiSabito | 600/391 |
| 5,199,432 | A * | 4/1993 | Quedens et al. | 600/376 |
| 5,289,827 | A * | 3/1994 | Orkin et al. | 600/588 |
| 5,373,852 | A * | 12/1994 | Harrison et al. | 600/546 |
| 5,406,961 | A * | 4/1995 | Artal | 600/591 |
| 5,471,993 | A * | 12/1995 | Yoches et al. | 600/591 |
| 5,483,970 | A * | 1/1996 | Rosenberg | 600/546 |
| 5,546,953 | A | 8/1996 | Garfield | |
| 5,623,939 | A * | 4/1997 | Garfield | 600/546 |
| 5,634,476 | A * | 6/1997 | Orkin et al. | 600/588 |
| 5,776,073 | A * | 7/1998 | Garfield et al. | 600/546 |
| 5,851,188 | A * | 12/1998 | Bullard et al. | 600/448 |
| 5,865,733 | A * | 2/1999 | Malinouskas et al. | 600/300 |
| 5,876,357 | A * | 3/1999 | Tomer | 600/591 |
| 5,913,834 | A * | 6/1999 | Francais | 600/591 |
| 5,978,693 | A * | 11/1999 | Hamilton et al. | 600/391 |
| 6,024,701 | A * | 2/2000 | Almog | 600/300 |
| 6,093,151 | A * | 7/2000 | Shine et al. | 600/485 |
| 6,270,458 | B1 * | 8/2001 | Barnea | 600/438 |
| 6,290,657 | B1 * | 9/2001 | Adams et al. | 600/591 |
| 6,440,089 | B1 * | 8/2002 | Shine | 600/591 |
| 6,610,012 | B2 | 8/2003 | Mault | 600/437 |
| 6,751,498 | B1 * | 6/2004 | Greenberg et al. | 600/511 |
| 6,912,414 | B2 * | 6/2005 | Tong | 600/372 |
| 7,144,379 | B2 * | 12/2006 | Belli | 600/588 |
| 7,532,923 | B1 * | 5/2009 | Hayes-Gill et al. | 600/511 |
| 7,616,980 | B2 * | 11/2009 | Meyer | 600/382 |
| 7,753,860 | B1 * | 7/2010 | Smith | 600/588 |
| 7,758,522 | B2 * | 7/2010 | Pandit | 600/591 |
| 7,831,302 | B2 * | 11/2010 | Thomas | 600/546 |
| 7,850,625 | B2 * | 12/2010 | Paltieli et al. | 600/588 |
| 7,869,863 | B2 * | 1/2011 | Moses et al. | 600/511 |
| 8,075,500 | B2 * | 12/2011 | Berger et al. | 600/591 |
| 8,160,692 | B2 * | 4/2012 | Principe et al. | 600/547 |
| 8,180,425 | B2 | 5/2012 | Selvitelli | |
| 8,292,831 | B2 * | 10/2012 | Fausett et al. | 600/588 |
| 8,460,217 | B2 * | 6/2013 | Shakiba | 600/591 |
| 8,892,181 | B2 | 11/2014 | Wolfberg | |
| 2003/0171661 | A1 * | 9/2003 | Tong | 600/300 |
| 2004/0010210 | A1 * | 1/2004 | Avinash et al. | 600/595 |
| 2005/0119583 | A1 * | 6/2005 | Fuller et al. | 600/511 |
| 2005/0267376 | A1 * | 12/2005 | Marossero et al. | 600/511 |
| 2005/0267377 | A1 * | 12/2005 | Marossero et al. | 600/511 |
| 2006/0074329 | A1 | 4/2006 | Ferguson, II et al. | |
| 2006/0149168 | A1 * | 7/2006 | Czarnek | 600/591 |
| 2007/0191728 | A1 | 8/2007 | Shennib | |
| 2007/0213627 | A1 * | 9/2007 | James et al. | 600/511 |
| 2007/0233203 | A1 | 10/2007 | Euliano et al. | |
| 2007/0255184 | A1 * | 11/2007 | Shennib | 600/591 |
| 2008/0082024 | A1 | 4/2008 | Meyer | |
| 2008/0154155 | A1 * | 6/2008 | Nishihara et al. | 600/595 |
| 2009/0036787 | A1 * | 2/2009 | James et al. | 600/511 |
| 2009/0054797 | A1 * | 2/2009 | Miller et al. | 600/511 |
| 2009/0062683 | A1 * | 3/2009 | Calderon et al. | 600/546 |
| 2009/0143650 | A1 * | 6/2009 | Guion-Johnson et al. | 600/301 |
| 2009/0270767 | A1 * | 10/2009 | Nishihara et al. | 600/595 |
| 2009/0299212 | A1 * | 12/2009 | Principe et al. | 600/547 |
| 2010/0274145 | A1 * | 10/2010 | Tupin et al. | 600/511 |
| 2011/0112440 | A1 | 5/2011 | Euliano | |
| 2011/0190652 | A1 | 8/2011 | Fink et al. | |
| 2011/0251512 | A1 * | 10/2011 | Fink et al. | 600/546 |
| 2011/0306862 | A1 * | 12/2011 | Hayes-Gill et al. | 600/382 |
| 2011/0306893 | A1 * | 12/2011 | Harrold et al. | 600/511 |
| 2012/0071744 | A1 | 3/2012 | Euliano | |
| 2012/0083676 | A1 * | 4/2012 | Wolfberg et al. | 600/301 |
| 2012/0116198 | A1 * | 5/2012 | Veen et al. | 600/372 |
| 2012/0130239 | A1 * | 5/2012 | Meyer et al. | 600/437 |
| 2013/0102856 | A1 | 4/2013 | Wolfberg | |
| 2013/0137998 | A1 * | 5/2013 | Lange et al. | 600/483 |

FOREIGN PATENT DOCUMENTS

| | | |
|---|---|---|
| EP | 2 016 894 A1 | 1/2009 |
| GB | 0810843.3 A | 6/2008 |
| GB | 2445454 A | 7/2008 |
| GB | 0819887.1 A | 10/2008 |
| JP | 2002153434 A | 5/2002 |
| JP | 2006198403 A | 8/2006 |
| JP | 2007195973 A | 8/2007 |
| JP | 2007296266 | 11/2007 |
| WO | 199308534 A1 | 4/1993 |
| WO | 2004047632 A1 | 6/2004 |
| WO | 2004072822 A2 | 8/2004 |
| WO | 2004084087 A1 | 9/2004 |
| WO | 2007066270 A2 | 6/2007 |
| WO | 2007110625 A2 | 10/2007 |
| WO | 2008073491 A1 | 6/2008 |
| WO | 2009/013701 A2 | 1/2009 |
| WO | 2009073964 A1 | 6/2009 |

OTHER PUBLICATIONS

Steer et al., "Electrical Activity of the Human Uterus in Labor, The Electrohysterograph," Amer J Obst Gynec, 59, p. 25-40 (1950).

Gondry et al., "Electrohysterography during pregnancy: preliminary report," Biomed Instrum Technol., Jul./Aug. 1993, 27(4), p. 318-324.

Devedeux et al., "Uterine electromyography: A critical review," Am J Obstet Gynecol, Dec. 1993, p. 1636-1644.

Marque et al., "Uterine EHG Processing for Obstetrical Monitoring," IEEE Trans Biomed Eng, p. 1182-1186, Dec. 1986, vol. BME-33, No. 12.

Nagel et al., "Processing of Abdominal Lead Ecg and Emg in Perinatal Monitoring", Physics in Medicine and Biology, vol. 5, iss 5, p. 959, 1980.

British Intellectual Property Office, Search Report issued in connection with Patent Application No. GB0911685.6, Claim 19, dated Jan. 12, 2011.

Monica Healthcare website, available at: http://www.monicahealthcare.com/index.php [accessed Oct. 26, 2009]. See especially Monica AN24 and News Archive pages.

Monica Healthcare website dated May 26, 2008 available at: http://web.archive.org/web/20080526045815/http://www.monicahealthcare.com/index.php.

British Intellectual Property Office, Examination Report issued in connection with Patent Application No. GB0911685.6 dated May 13, 2010.

Monica Healthcare Limited, Response to Examination Report (issued in connection with Patent Application No. GB0911685.6 dated May 13, 2010) dated Nov. 11, 2010.

British Intellectual Property Office, Examination Report issued in connection with Patent Application No. GB0911685.6 dated Jan. 13, 2011.

Monica Healthcare Limited, Response to Examination Report (issued in connection with Patent Application No. GB0911685.6 dated Jan. 13, 2011) dated May 11, 2011.

British Intellectual Property Office, Examination Report issued in connection with Patent Application No. GB0911685.6 dated Jun. 1, 2011.

(56) References Cited

OTHER PUBLICATIONS

Monica Healthcare Limited, Response to Examination Report (issued in connection with Patent Application No. GB0911685.6 dated Jun. 1, 2011) dated Aug. 2, 2011.
British Intellectual Property Office, Combined Search and Examination Report issued in connection with Patent Application No. GB1107754.2 dated Jun. 1, 2011.
Monica Healthcare Limited, Response to Combined Search and Examination Report (issued in connection with Patent Application No. GB1107754.2 dated Jun. 1, 2011) dated Dec. 2, 2011.
Rai et al., "Symphysis fundal height curve—a simple method for foetal growth assessment," Journal of PG Medicine, 1995, vol. 41, Issue 4, pp. 93-94.
British Intellectual Property Office, Search Report issued in connection with Patent Application No. GB0911685.6, Claims 20-22, dated Jan. 12, 2011.
British Intelelctual Property Office, Search Report issued in connection with Patent Application No. GB0911685.6, Claims 1-18, dated Oct. 29, 2009.
European Patent Office / ISA, International Search Report and Written Opinion of the ISA issued in connection with Patent Application No. PCT/GB2010/001294 dated Jul. 3, 2013.
Chiara Rabotti et al., "Estimation of internal uterine pressure by joint amplitude and frequency analysis of electrohysterographic signals; Estimation of internal uterine pressure by joint amplitude and frequency analysis," Physiological Measurement, Institute of Physics Publishing, Bristol, GB, vol. 29, No. 7, Jul. 1, 2008 (Jul. 1, 2008), p. 829-841, XP020137166, ISSN: 0967-3334, p. 831-834, 836.
Rabotti C. et al., "Relationship between electrohysterogram and internal uterine pressure: a preliminary study," Conference Proceedings, Annual International Conference of the IEEE Engineering in Medicine and Biology Society (IEEE Cat. No. 06CH37748); Aug. 30-Sep. 3, 2006; New York, NY, USA, IEEE, Piscataway, NJ, USA, Aug. 30, 2006, p. 1661-1664, XP031390100, ISBN: 978-1-4244-0032-4.
British Intellectual Property Office, Search Report issued in connection with Patent Application No. GB1107754.2, Claims 1-4, dated May 31, 2011.
European Patent Office / ISA, International Preliminary Report on Patentability on Application No. PCT/GB2010/001294, dated Mar. 19, 2013.

* cited by examiner

Analysis

Overall:
Frames analysed: 18/18
FHR: Mean 139.76bpm, Basal 139.69bpm
Accelerations: 39(28 Small, 11 Large), Decelerations: 1
Mean STV:6.34 ms
MMR:38.94 ms
High var: 44.26%(44.71 ms), Low var: 9.07%(23.93 ms)

| Frame length (minute): | 30 | Acceleration (s): | 15 | Deceleration I (s): | 60 |
| Max frame loss (%): | 50 | Large acceleration (bpm): | 15 | Deceleration I (bpm): | 10 |
| Var low threshold (ms): | 30 | Small acceleration (bpm): | 10 | Deceleration II (s): | 30 |
| Var high threshold (ms): | 32 | | | Deceleration II (bpm): | 20 |

Frame by frame:

| Time(H:M) | Loss (%) | Mean (bpm) | Basal (bpm) | Small Acc | Large Acc | Decel | STV (ms) | MMR (ms) | High var (%) | High var (ms) | Low var (%) | Low var (ms) |
|---|---|---|---|---|---|---|---|---|---|---|---|---|
| 22:28 | 00.21 | 142.86 | 141.37 | 1 | 4 | 0 | 7.17 | 47.47 | 80.00 | 52.19 | 0.00 | - |
| 22:58 | 29.79 | 151.31 | 154.18 | 4 | 1 | 1 | 7.66 | 45.73 | 26.67 | 44.48 | 0.00 | - |
| 23:28 | 05.21 | 144.75 | 144.64 | 2 | 1 | 0 | 7.83 | 38.71 | 46.67 | 41.57 | 0.00 | - |
| 23:58 | 00.63 | 140.39 | 140.23 | 0 | 0 | 0 | 7.48 | 38.15 | 16.67 | 38.13 | 0.00 | - |
| 00:28 | 00.00 | 143.31 | 141.26 | 2 | 0 | 0 | 4.90 | 30.31 | 0.00 | - | 43.33 | 24.69 |
| 00:58 | 00.00 | 141.30 | 141.32 | 2 | 2 | 0 | 5.55 | 35.52 | 70.00 | 40.29 | 0.00 | - |
| 01:28 | 00.00 | 138.29 | 138.26 | 2 | 1 | 0 | 4.59 | 31.36 | 43.33 | 41.18 | 30.00 | 21.78 |
| 01:58 | 00.00 | 138.62 | 138.43 | 1 | 0 | 0 | 5.83 | 34.90 | 30.00 | 40.05 | 16.67 | 25.52 |
| 02:28 | 00.00 | 138.68 | 139.87 | 3 | 1 | 0 | 6.51 | 36.90 | 56.67 | 44.92 | 20.00 | 24.55 |
| 02:58 | 00.00 | 138.16 | 136.60 | 1 | 0 | 0 | 5.55 | 33.43 | 50.00 | 38.83 | 33.33 | 23.03 |
| 03:28 | 00.00 | 133.40 | 132.99 | 0 | 0 | 0 | 8.08 | 50.67 | 100.00 | 50.67 | 0.00 | - |
| 03:58 | 00.00 | 139.64 | 138.93 | 2 | 1 | 0 | 5.95 | 37.67 | 23.33 | 46.27 | 0.00 | - |
| 04:28 | 00.00 | 137.89 | 138.21 | 1 | 0 | 0 | 6.13 | 42.62 | 70.00 | 48.87 | 0.00 | - |
| 04:58 | 00.00 | 135.70 | 135.58 | 0 | 0 | 0 | 6.92 | 39.86 | 53.33 | 43.11 | 0.00 | - |
| 05:28 | 00.00 | 138.62 | 138.45 | 0 | 0 | 0 | 5.12 | 31.65 | 23.33 | 38.09 | 0.00 | - |
| 05:58 | 00.00 | 136.76 | 136.82 | 3 | 0 | 0 | 6.75 | 41.78 | 23.33 | 56.96 | 0.00 | - |
| 06:28 | 00.21 | 138.75 | 138.25 | 4 | 0 | 0 | 5.80 | 35.86 | 46.67 | 38.78 | 0.00 | - |
| 06:58 | 00.00 | 137.21 | 138.98 | 0 | 0 | 0 | 6.29 | 48.38 | 36.67 | 40.82 | 20.00 | 25.08 |

Analyse   Save   Print   OK

*Fig. 2*

Output after step 407

Output after step 409

Output after step 413

MONITORING UTERINE ACTIVITY

The present invention relates to apparatus and a method suitable for long term monitoring and detection of the health of a human fetus and the mother during pregnancy, during both of the antenatal and intrapartum periods.

Auscultation, the ability to listen to internal sounds of the human body, has been a well known method to detect the beating human heart for many centuries. The use of the technique to diagnose fetal life was first developed in the early 19th century by Laennec with the invention of the stethoscope in 1816. This heralded a period of further development of stethoscopic auscultation as its potential for highlighting fetal wellbeing by monitoring the fetal heart rate (FHR) was recognised clinically. It was apparent that changes in FHR could provide indications as to what point obstetric intervention may help reduce instances of intrapartum fetal death. In 1876 Pinard introduced his version of a fetal stethoscope, which is still used today, and the criteria, which were set around this time, for what is normal FHR remained virtually unchanged for the next 70 years. By the start of the 20th century it had become common practice to monitor FHR by auscultation.

Early abdominal electrocardiographic techniques using cutaneous electrodes placed on the mother's abdomen were unable to successfully discard maternal rhythms (i.e. the maternal ECG). This issue was only avoided in 1960 by the introduction of the fetal scalp electrode. In this case a scalp clip electrode is lightly attached to the baby's head. However, this can only be used when the mother's membranes have ruptured.

Further advances were made in the 1960s by use of the Doppler effect. Here, the change in frequency of a wave, as perceived by an observer moving relative to the source of the wave, was applied to detecting the FHR. Four years later the first commercially available electronic fetal monitor (EFM) using Doppler ultrasound was introduced.

The Doppler ultrasound technique consists of directing a 2 MHz (or other similar frequency) crystal transducer at the fetus on the mother's abdomen. The signal reflected from the fetus is shifted by a small frequency (known as the Doppler shift) which is due to the pulsation of the fetal heart and hence after suitable processing a fetal heart rate (fHR) trace is generated. Portable Doppler systems exist but as with all single channel Doppler systems the transducer has to be periodically re-positioned to point at the fetal heart and this requires the intervention of clinically trained staff. Such systems are therefore limited to use in a hospital environment for short periods. Further, the Doppler ultrasound technique only provides an averaged fHR and gives no information about: beat-to-beat variability; morphology such as contained in the shape of a fetal electrocardiogram (fECG) complex; uterine contractions; variation of these parameters over long periods of time.

Shono et al "Fetal heart rate recorder for long-duration use in active full-term pregnant women", Jnl of Obstetrics and Gynecology, 1994 83, 2 described a multi-channel Doppler system consisting of 6 ultrasound transducers positioned on the mother's abdomen so as to monitor the fetal heart wherever the fetus move within the uterus. However, this was cumbersome and although longitudinal studies of averaged fetal heart rate variability (fHRV) were possible the technique is invasive and worries exist about continual ultrasound insonation of the fetus.

Combining fetal blood acid-base monitoring in conjunction with electronic monitoring of the FHR (via either fetal scalp ECG or Doppler ultrasound) allowed an increase in FHR specificity and directly led to a rapid increase in the obstetric use of continuous electronic FHR monitoring by the late 1960s.

Intermittent auscultation using the Pinard stethoscope and EFM, usually by way of a hand-held Doppler monitor, are utilised to monitor the fetus during the antenatal period. During labour, however, it is found that the monitoring of the fetus, following an uncomplicated pregnancy, is by way of intermittent auscultation. In some countries and geographical regions, continuous EFM can be used for those pregnancies considered to be of high risk whilst in other countries such techniques are considered routine. Occasionally, it is necessary to use a more accurate FHR modality by utilising a fetal scalp electrode but of course this can only occur during the intrapartum period (i.e. when the mother's membranes are broken during labour) and can lead to infections.

The interpretation of the EFM 2 second (and 3.75 second) average fetal heart rate readings is highly subjective. Some countries use bespoke software for determining short term variation (STV), number of accelerations/decelerations etc. Others have used and/or adapted the algorithms of Dawes and Redman (System 8002). This analysis software is usually deployed during the antenatal period and hence not during labour and delivery. The very fact that Doppler ultrasound-acquired fetal heart rate data is an average over epochs as long as 3.75 seconds means that higher frequency variability is removed. Hence, no knowledge is gained of the true beat-to-beat variability. As a result the STV technique can lack sensitivity in assessing the onset of fetal distress. Consequently, fetal blood sampling (FBS) is often used during problematic labour. Here, a small amount of blood is taken from the scalp of the fetus. The level of oxygen present in the sample directly indicates the assessment of fetal wellbeing. However, infections can occur.

Often the ability to undertake a fetal blood sample is restricted due to the fact that the mother is in the antenatal period and the ability to routinely reach the fetus is not possible since the membranes are not ruptured. Further, the recording of continual FHR is difficult to undertake with Doppler ultrasound due to the movement of the transducer and the invasive nature of the ultrasound transducer. Hence the progression of the 3.75 second (or 2 second) SW cannot be tracked without continual clinical supervision. This problem is exasperated by the fact that the beat-to-beat SW (referred to here as the true SW (TSTV) is not measurable with Doppler cardiotocographs. TSTV is measured using the adult ECG equivalent of: RMSSD (i.e. root mean square of the successive differences of the RR time intervals); spectral analysis of the beat-to-beat data; multiscale entropy analysis etc. Such parameters in adults indicate the wellbeing of the adult neurofunction reflecting sympathetic and parasympathetic activity and hence this could potentially map onto fetal development and fetal wellbeing.

A further significant parameter that is also routinely monitored is the activity or contractions of the maternal uterus, simply referred to as the uterine activity (UA). Monitoring the UA of the maternal abdomen allows the clinician to assess that the fetus is able to withstand the effects of each contraction. During a contraction the placental blood supply is momentarily interrupted. While most fetuses cope well with this interruption of blood supply there are some fetuses (i.e. those who have not matured physically during pregnancy or whose mothers have pre-eclampsia etc) that will find it more difficult. UA is therefore an effective method for measuring fetal risk and hence fetal wellbeing.

UA can be measured by monitoring the maternal intrauterine pressure (IUP) caused by contractions of the uterine muscle. This IUP is measured by placing an internal pressure transducer inside the uterus. However, this technique is invasive and can only be carried out once the mother's membranes have broken.

A common non-invasive method for recording the UA is by way of cardiotocograph (CTG) which aims to assist the clinician in detecting fetal hypoxia during labour. The CTG produces a record of both the uterine contractions (toco) and the FHR (cardio), the latter parameter in the form of a 2 second or 3.75 second average. The FHR is detected using a Doppler ultrasound transducer placed on the maternal abdomen. The UA is measured with the use of a second external transducer (a strain gauge referred to as a tocodynometer) placed on the abdomen of the mother. However, the use of both the external strain gauge tocodynometer and the ultrasound transducer can be uncomfortable for the mother and is often unreliable when used on obese women.

By way of a summary, the recording of the fetal heart rate is usually carried out with a Doppler ultrasound CTG machine which also detects contractions using an external abdominal pressure transducer. The heart rate detected from the ultrasound transducer is in the form of a 2 or 3.75 second average and does not reveal the true beat-to-beat variability. In addition the CTG is both cumbersome and uncomfortable for the mother as it contains two relatively large transducers which are attached to the mother with an elasticated belt.

Abdominal Electrophysiology During Pregnancy

A highly suitable, non invasive and unobtrusive technique can be used during pregnancy by placing cutaneous electrodes on the maternal abdomen. These electrodes when correctly positioned can detect both the maternal (mECG) and fetal ECG (fECG) as well as a signal called the electrohysterogram (EHG). The EHG is a direct result of the contractions of the uterus.

Hence in a single pair of abdominal electrodes it is possible to detect fetal heart rate, uterine activity and maternal heart rate, and thereby provide a CTG apparatus that is both portable and unobtrusive for the mother.

The EHG detected by these abdominal electrodes in reality is detecting the uterine electromyogram (EMG) signal. This signal was detected as early as 1950 (Steer and Hertsch, Amer J Obst Gynec, 59, 25 (1950). Gondry et al (1993) reported that the EHG can be detected from the 18th week of pregnancy and that its amplitude increases from that point onwards. Devedeux et al, Am J Obstet Gynecol, 1993, "Uterine Electromyography: A Critical Review" reported that the increase in IUP, measured by using an internal pressure transducer placed within the uterus, occurs in synchronisation with the indirect EHG measurement.

Marque et al "Uterine EHG Processing for Obstetrical Monitoring" IEEE Trans Biomed Eng, pp 1182-1186, December 1986, vol. BME-33, No. 12 reported that the EHG contains two signals—a slow wave and a fast wave. The slow wave ranges from 0.01 to 0.03 Hz with an amplitude between 0.5 mV and 15 mV. The fast wave varies from 0.2 to 3 Hz with amplitude between 0.02 mV and 0.5 mV respectively. It is the slow wave that is in synchronisation with the IUP and the fast wave is superimposed on the slow wave in the form of an amplitude modulated signal. The frequency of the fast wave can be further subdivided into a low frequency band (0.2 Hz to 0.8 Hz) always present in every contraction and a high frequency band (0.8 to 3 Hz) related to efficient parturition contractions. The conclusion here was that only when abdominal activity is observed in the frequency band corresponding to the slow wave modulated by the fast wave can it be said to be demonstrative of genuine uterine EMG activity.

Nagel and Schaldach, "Processing Of Abdominal Lead Ecg And Emg In Perinatal Monitoring", Physics In Medicine And Biology, vol 5, iss 5, p 959, 1980 reported that the suppression of interference from the maternal and fetal ECGs is feasible. They argued that this is possible when utilising much higher frequency components (150 Hz to 250 Hz) than are normally recognised as being part of the EHG. In this way, components of the EMG of the abdominal wall can be measured and it is claimed that contractions in this area also contribute to an increase in IUP.

In general, whatever measurement technique is utilised to record UA, it is quantified by the number of contractions per unit time. During the initial phase of the first stage of labour the ideal frequency would be 2 or 3 contractions in each ten minute period. This contraction rate would increase to 4 or 5 in the same time period during the latter phase of the first stage. Contractions occurring less frequently often leads to a more lengthy labour. The fetus is at greater risk if this is the case. Conversely, a contraction rate in excess of 5 every ten minutes may adversely affect the ability of the fetus to reoxygenate itself between contractions.

A quantifiable measure of contractions is that defined by the Montevideo units. These were created in 1949 by Roberto Barcia and Hermogenes Alvarez, from Montevideo, Uruguay. Units are calculated by measuring uterine pressure above baseline and multiplying by the number of contractions in a 10 minute period. In order to obtain this measure the uterine pressure must be measured through an intrauterine pressure catheter. For example if uterine pressure is 50 mmHg above baseline and during a 10 minute period of measurement 4 contractions occur then the total Montevideo units (MVUs) are 200 MVUs. Generally, values above 200 MVUs are considered necessary for adequate labour during stage 2. These units therefore indicate both contraction count and contraction strength (mmHg).

It is also important to ascertain the efficiency of the contractions. A factor in assessing the contraction efficiency is the duration of the contractions. Initially, in the first stage of labour they may be of 30 to 60 seconds in duration. This may increase to 90 seconds during latter phases of the first stage and the second stage.

Although it is only possible to measure contraction intensity directly by utilising an IUP sensor, manual assessment (palpation) of uterine tone and basal tone can yield important information to aid assessment during oxytocin infusion and if there is a suspected placental abruption. The contraction intensity can also be measured from the electrohysterogram in terms of the magnitude of the resulting EHG signal in terms of the peak magnitude of detected EMG voltage.

If IUP exceeds 30 mmHg, placental blood flow will be temporarily blocked and this will cause an interruption to the gas exchange between fetus and mother. Following such an interruption the fetus requires between 60 and 90 seconds to regain normal blood gases. The fetus's predisposition to overcome the stress of labour often equates to its ability to deal with changes that occur during contractions. The length of labour and, by implication, the length of time during which the fetus is exposed to occasional, possibly hypoxic instances is one key issue closely related to intrapartum hypoxia. In the second stage the length of time the mother is actively pushing should of course always be taken into account when assessing the risk of intrapartum hypoxia.

Longitudinal Non Stress Tests—in the Antenatal Period

Several techniques are available for the obstetrician to assess fetal health in the antenatal period. These are summarised below:

1. Contraction Stress Test

Here the FHR is measured in response to contractions. These contractions are usually generated artificially by intravenous administration of oxytocins or external nipple stimulation. A poorly oxygenated fetus will show decelerations in the FHR.

2. Nonstress Test

FHR variability is measured with no artificial stimulation. FHR for a healthy fetus should undergo temporary accelerations at some stage during a recording of 20-40 minutes of data—called a reactive trace. Acoustic stimulation can be used to reduce the NST testing time.

3. Fetal Movement Assessment

The lack of fetal movements is a possible indication of fetal distress. Techniques to measure fetal movements include: kick counts recorded by the mother; ultrasound imaging; Doppler ultrasound; fetal ECG morphological changes; etc.

4. Biophysical Profile

This is a "score" assigned to the wellbeing of the fetus based upon: NST; fetal breathing movements; fetal body and limb movements; extension of fetal extremities; and the determination of amniotic fluid volume.

5. Modified Biophysical Profile

Measure of amniotic fluid volume as an index and is equal to the sum of fluid volumes in each of the four quadrants. This measure then combined with the NST score.

6. Umbilical Artery Doppler Velocimetry

This uses Doppler ultrasound imaging to measure blood flow in the umbilical cord. This measure indicates the level of oxygenation that is occurring to the fetus.

It would be advantageous to enable the automatic acquisition of a NST measure in a longitudinal manner over several hours combined with EHG and fetal movement. This would allow the observation of fetal disposition as a function of time and provides continual reassurance of fetal wellbeing. This is not possible with Doppler ultrasound CTG since this is an intermittent technique which is often 20 minute recordings each separated by 24 hours. This represents a severe undersampling and hence can miss the epochs of degraded FHR reactivity and decelerations.

The ability to detect fetal and maternal electrocardiograms using cutaneous electrodes placed on the maternal abdomen is adequately described by the patents EP 1220640 and EP 1680018. This technique allows long term FHR and MHR measurement using a 2 or 3.75 second average and hence offers an ideal method and apparatus for a NST but also for detecting these degraded epochs and hence provides a long term NST.

However, this technique lacks three important extraction parameters:

1. No inclusion of the UA contractions over short and long recordings
2. No summarised fetal heart rate data analysis
3. No inclusion of beat-to-beat RR measures such as: RMSSD, entropy, spectral content etc.

It is an object of the present invention to provide an improved apparatus and method for monitoring uterine activity. It is a further object of the invention to provide an apparatus and method that can be suitable for long term automatic monitoring of uterine activity. Some or all of the objects may be achieved by the apparatus and methods described herein.

According to one aspect, the present invention provides an apparatus for detecting uterine activity comprising:

first input means configured to receive electrical signals from cutaneous electrodes;

second input means configured to receive movement signals indicative of a movement of the maternal body from a movement detector;

signal processing means configured to separate a uterine electromyogram signal from fetal and maternal heart rate signals in the electrical signals and to filter maternal motion artefacts from the uterine electromyogram signal using the movement signals; and output means configured to present electrohysterogram (EHG) data from the uterine electromyogram signal.

According to another aspect, the present invention provides a method of detecting uterine activity comprising the steps of:

generating electrical signals from cutaneous electrodes disposed on a maternal abdomen;

obtaining movement signals indicative of a movement of the maternal body;

separating a uterine electromyogram signal from fetal and maternal heart rate signals in said generated electrical signals and filtering maternal motion artefacts from the uterine electromyogram signal using the movement signals; and providing electrohysterogram (EHG) data from the uterine electromyogram signal.

According to another aspect, the present invention provides an apparatus for detecting uterine activity comprising:

input means configured to receive electrical signals from cutaneous electrodes;

signal processing means configured to separate a uterine electromyogram signal from fetal and maternal heart rate signals in the electrical signals and to filter foetal motion artefacts from the uterine electromyogram; and output means configured to present electrohysterogram (EHG) data from the uterine electromyogram signal.

According to another aspect, the present invention provides a method of detecting uterine activity comprising the steps of:

generating electrical signals from cutaneous electrodes disposed on a maternal abdomen;

separating a uterine electromyogram signal from fetal and maternal heart rate signals in said generated electrical signals and filtering foetal motion artefacts from the uterine electromyogram; and providing electrohysterogram (EHG) data from the uterine electromyogram signal.

According to another aspect, the present invention provides an integrated electrode and movement sensor for attachment to a maternal abdomen configured to generate electromyogram signals from the maternal body and movement signals indicative of a movement of the maternal body, the electrode comprising:

an electrical contact portion for establishing electrical contact with the skin of the abdomen;

attachment means for securing the integrated electrode and movement sensor to the body; and a transducer configured to generate movement signals indicative of movement of the maternal body.

According to another aspect, the present invention provides apparatus for collecting fetal heart rate data and uterine activity data, comprising:

means for receiving, from sensors disposed on the abdomen of a pregnant mother, electrical signals indicative of fetal heart rate and uterine activity;

means for processing said signals to obtain at least one fetal heart rate parameter and at least one uterine activity parameter; and means for providing as output a graphical or tabular form of said at least one fetal heart rate parameter and said at least one uterine activity parameter for timed frames.

Embodiments of the present invention will now be described by way of example and with reference to the accompanying drawings in which.

The apparatus described here is capable of determining uterine activity in the form of contractions over short and long recording periods, providing summarised fetal heart rate data analysis and establishing beat-to-beat RR measures such as: RMSSD, entropy, spectral content etc. The reason why the addition of these parameters to automatic collection by a portable instrument is desirable is twofold.

Firstly, performing a non-stress test (NST) is in fact not possible without the presence of some indication of UA. This is because an acceleration or deceleration in heart rate is an indication of fetal behaviour. However, the fetus's behaviour responds differently when exposed to a contraction. Hence knowledge of the presence or not of a contraction is important in order to interpret heart rate variations correctly.

Secondly the ability to provide a continuous 24 hour record of fetal heart rate, maternal heart rate and uterine activity presents new challenges to the clinician. The enormity of the data set is such that clinicians are unable to absorb efficiently the general progression of the fetus and the data set may be open to subjective interpretation.

Figure 1A:
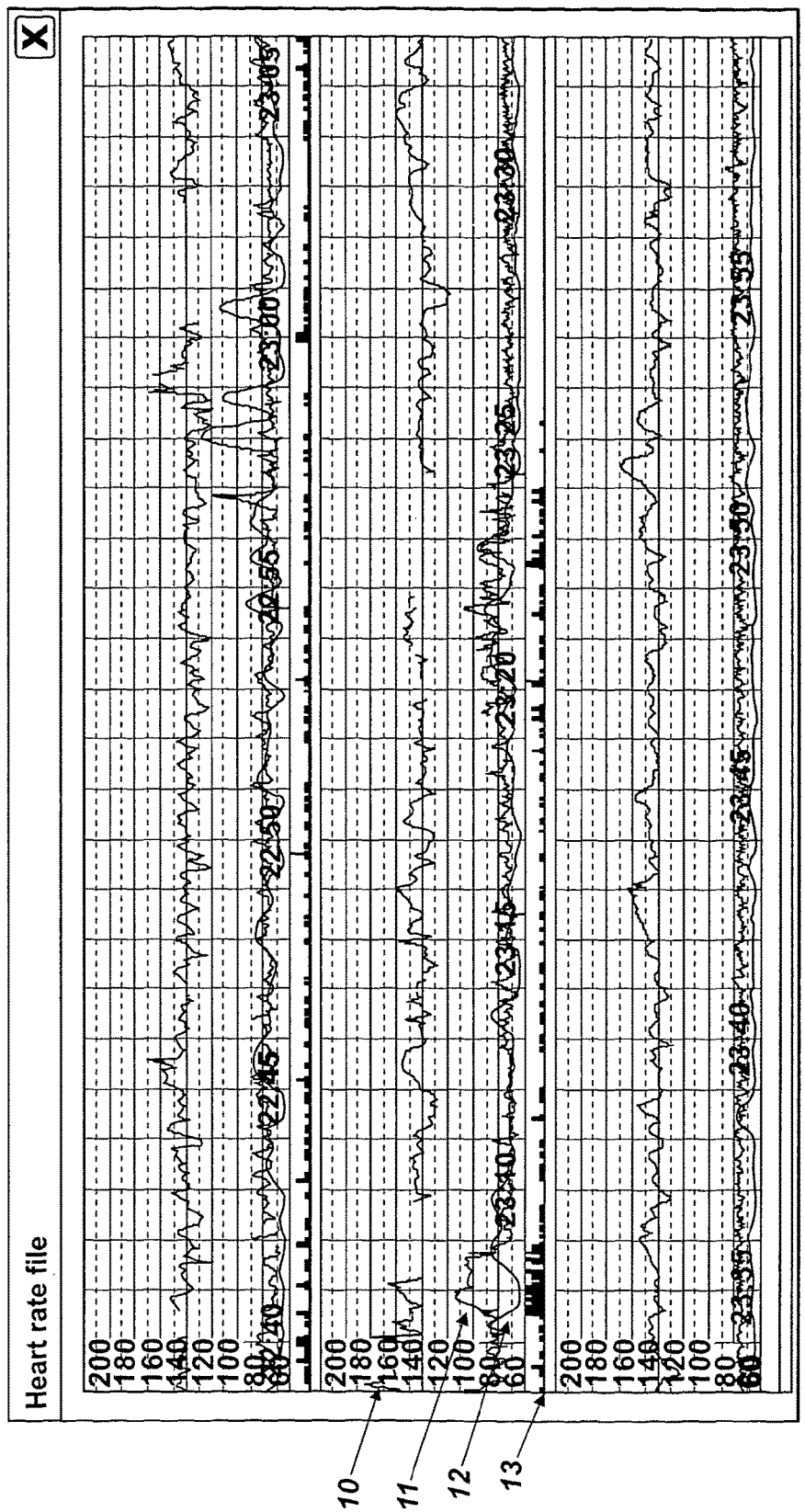
FIGS. 1a, 1b and 1c show charts of fetal heart rate (FHR), maternal heart rate (MHR), and uterine activity (UA) as measured by electrohysterogram (EHG) and maternal activity, taken over a period of approximately 9 hours.
Figure 1A:
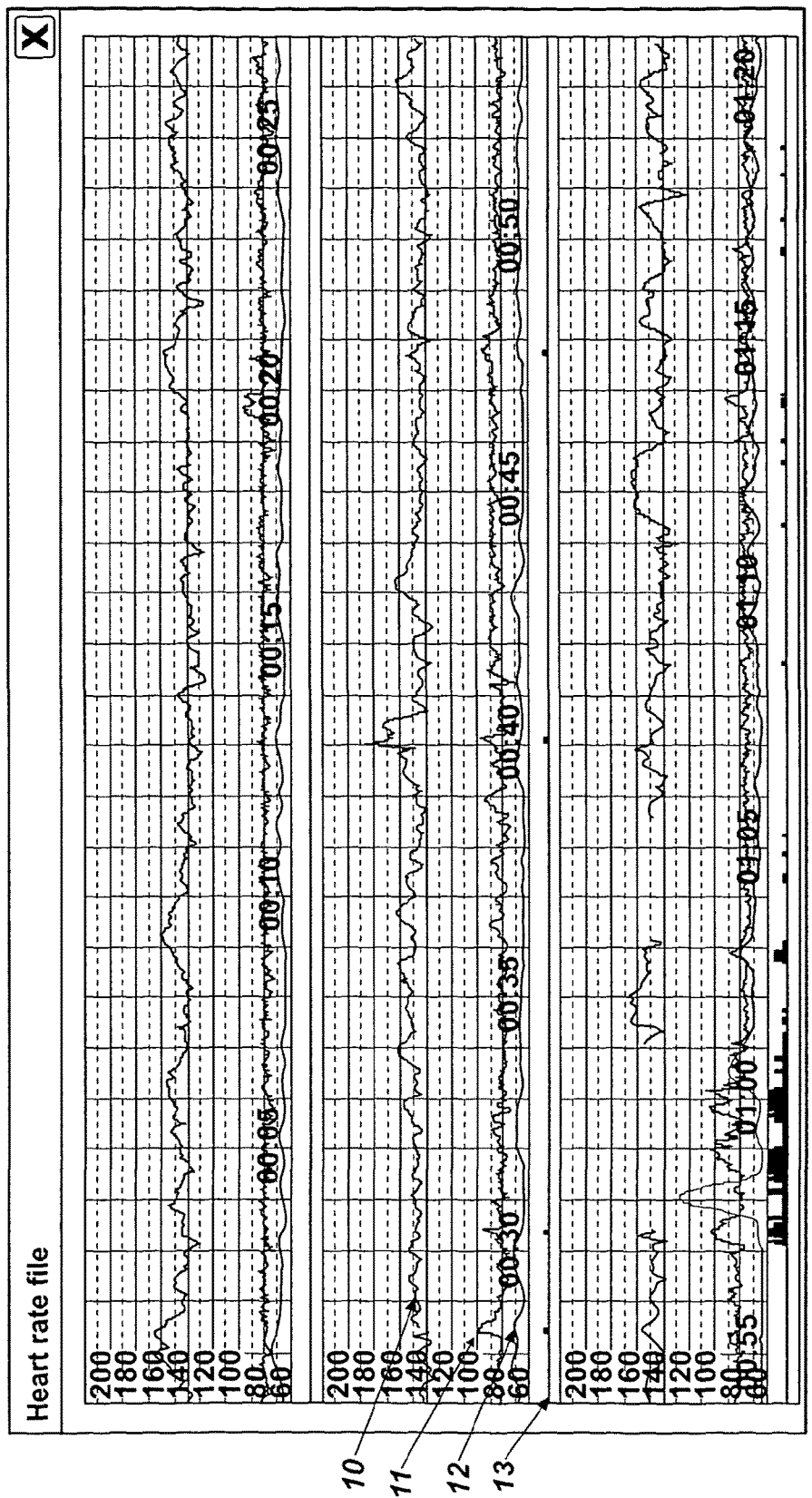
Figure 1B:
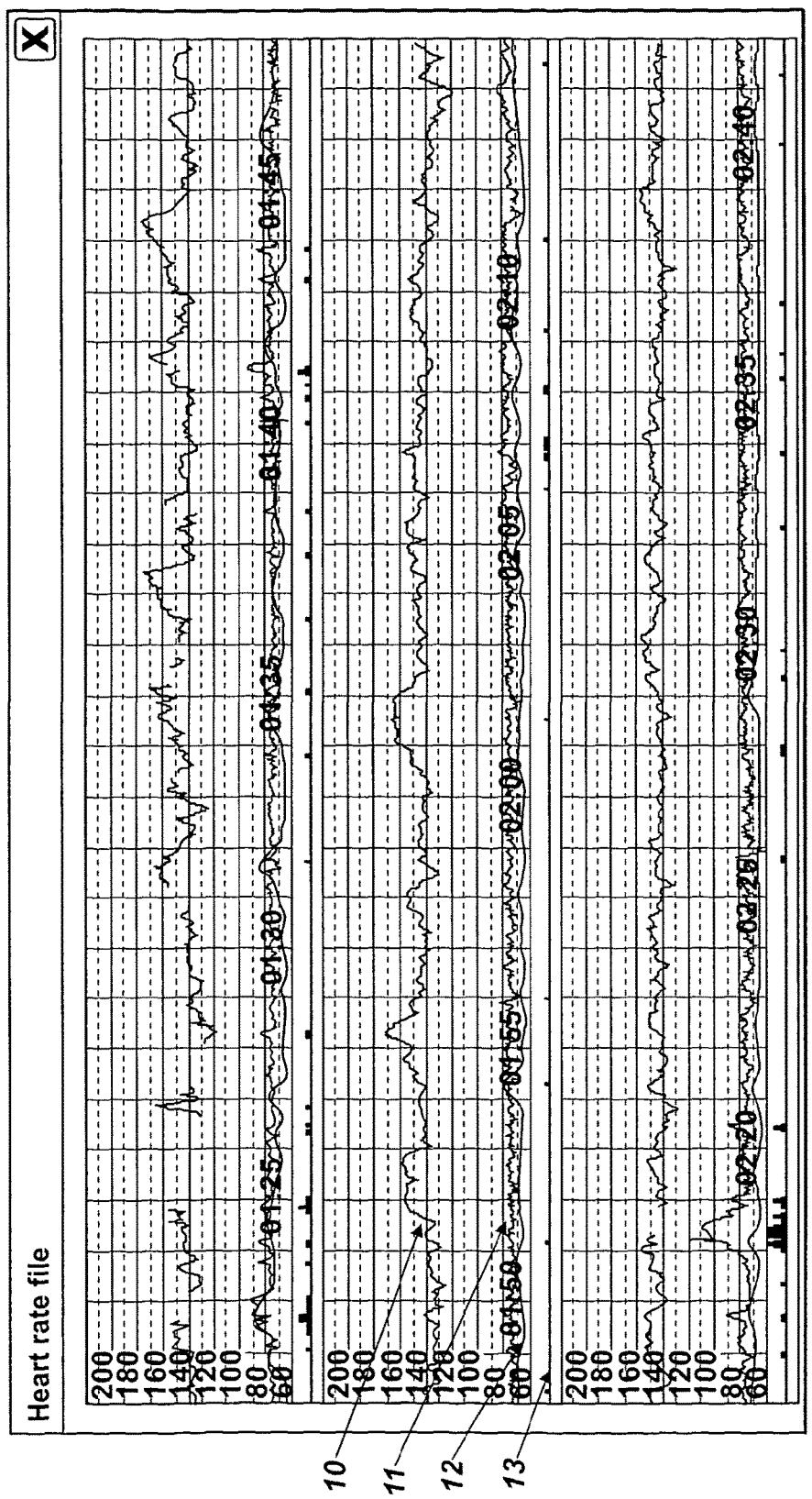
Figure 1B:
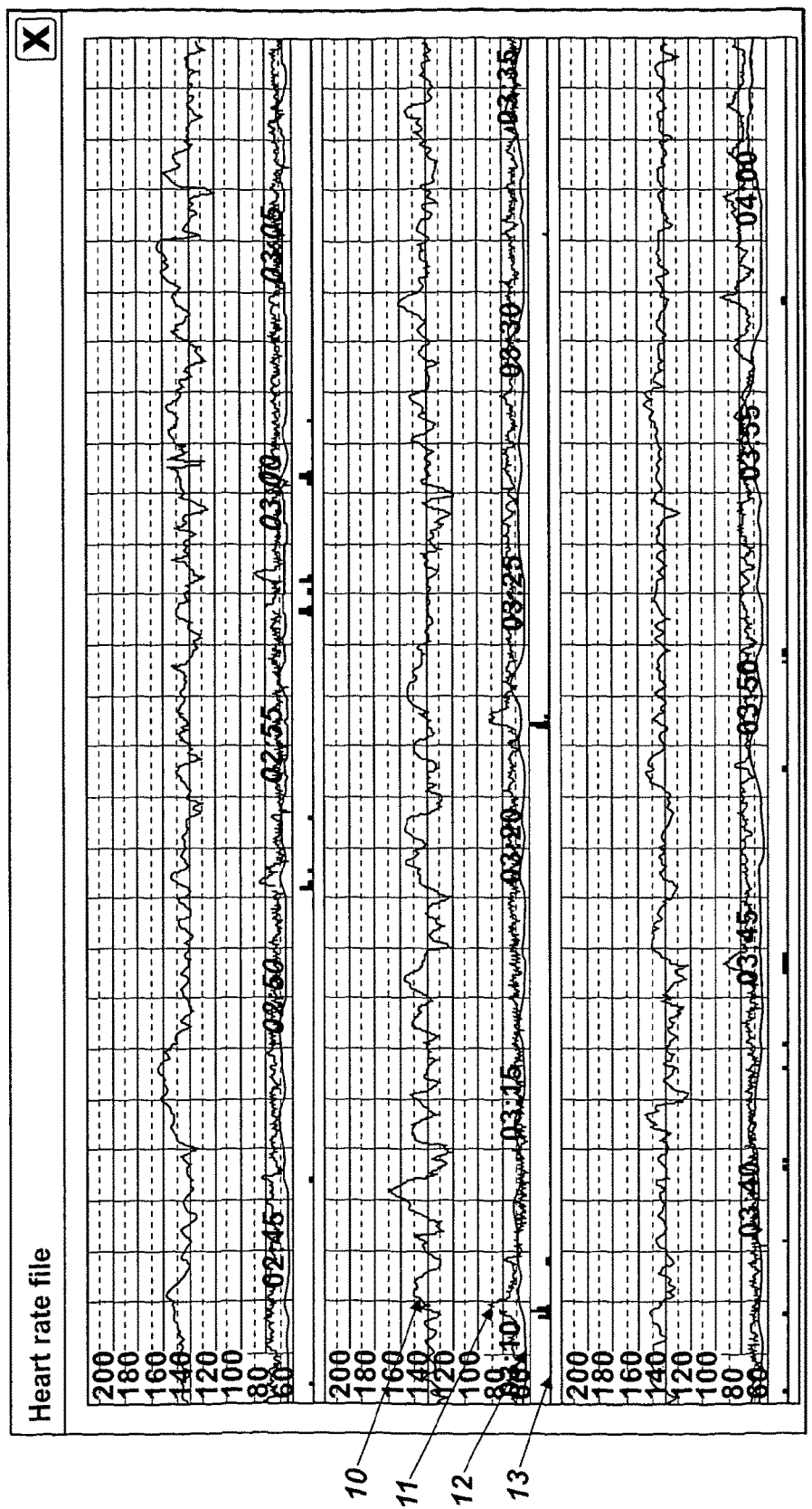
Figure 1C:
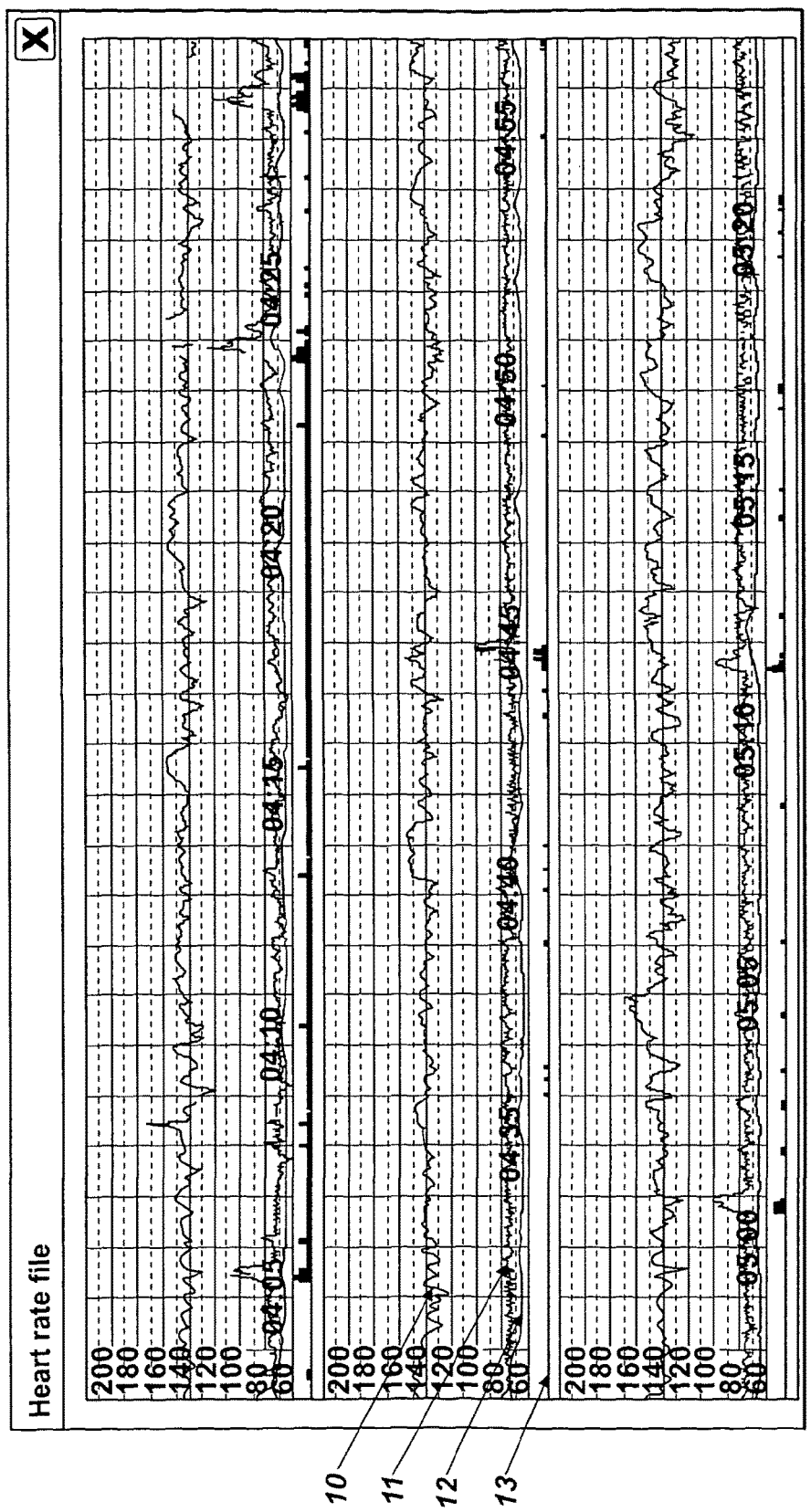
Figure 1C:
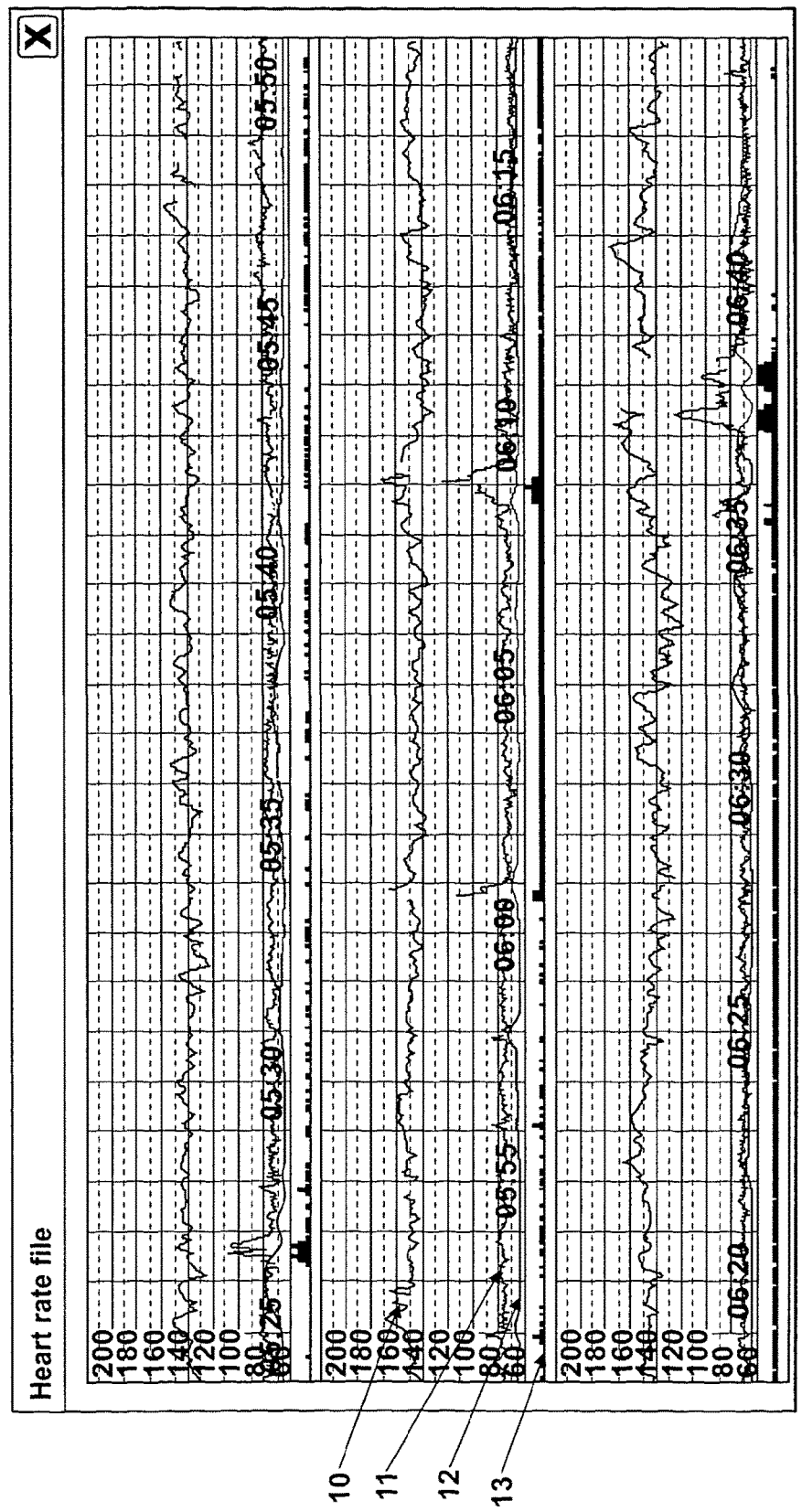

By way of illustration, FIGS. 1a, 1b and 1c, show FHR, MHR, EHG (UA) and maternal movement over approximately a 9 hour period. Trace 10 (i.e. the upper trace on all plots) represents the fetal heart rate in beats per minute (y axis) as a function of time (x axis). Similarly, trace 11 (i.e. the next lower trace on all plots) represents the maternal heart rate in beats per minute as a function of time. Trace 12 (i.e. the second lowest trace, near the x-axis) represents the uterine activity as determined from EHG data. Finally, trace 13 represents maternal activity as determined for example by an accelerometer placed inside the device or on the patient.

Figure 2:
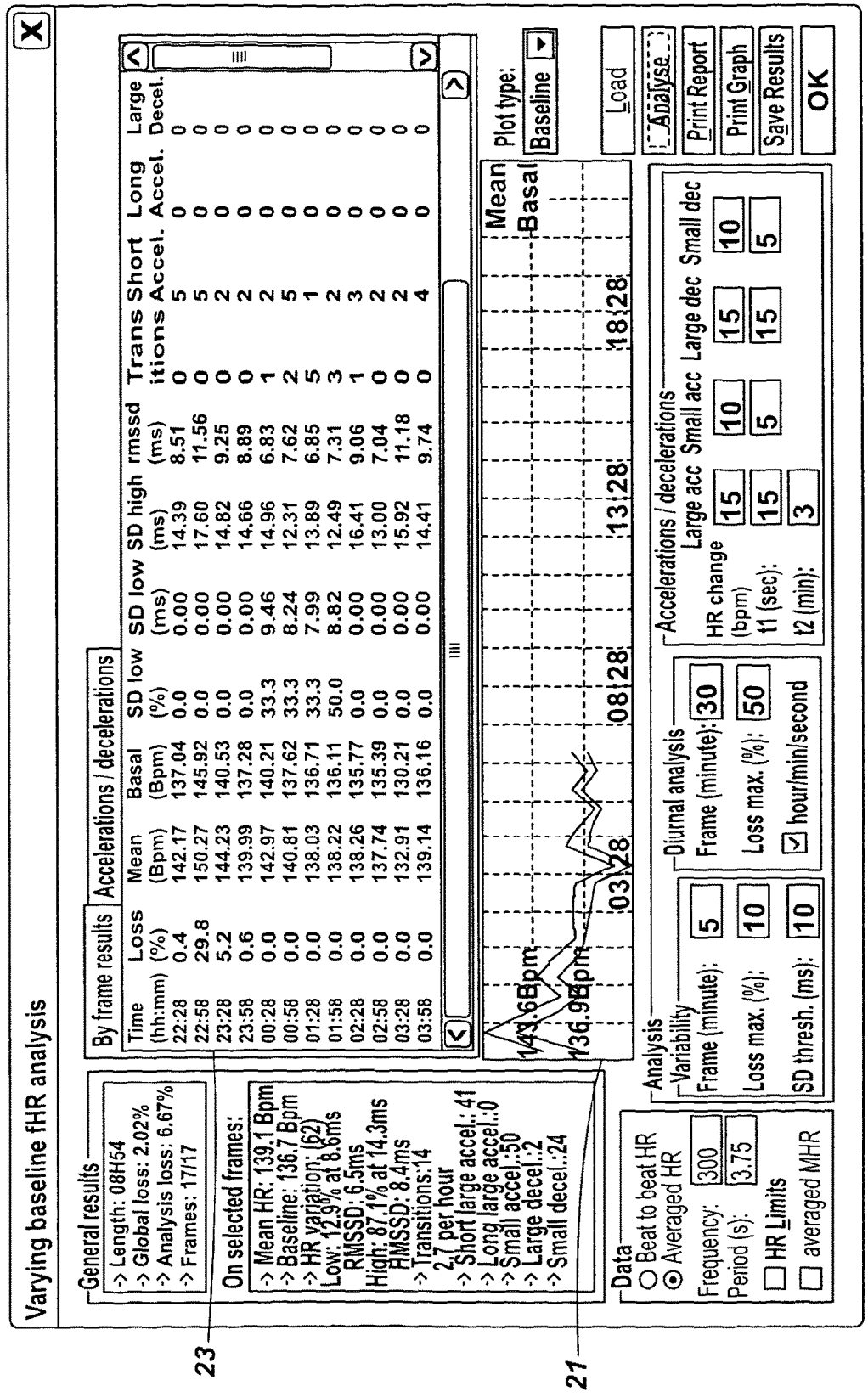
FIG. 2 shows a display of summarised analysis of data extracted from the data set shown in FIGS. 1a to 1c.

Summarising this data to the clinician provides a simpler and less subjective means of interpreting the data. FIG. 2 shows the same data as in FIG. 1 but represented in half hourly frames in chart 21 and the associated tables 22, 23. These tables and chart capture the FHR trace in a succinct manner and allow rapid assessment of the clinical status of the fetus. Two sets of tables 22, 23 are shown in FIG. 2.

Consider first the upper table 22 in FIG. 2. At the top left is a summary analysis 22a of the whole data record which gives the number of frames analysed (30 minutes each in this case, which can be set by the user), the mean FHR, the number of accelerations and decelerations, the mean Short Term Variability (STV) and the Mean Minute Range (MMR) etc.

STV is defined in any minute that does not contain a deceleration, then for each valid minute the SW is computed as the average of the difference of the adjacent 2 or 3.75 second epochs. These decelerations can also be defined by the user along the top 22b of the tables, e.g. 10 BPM drop in FHR over 60 seconds.

The MMR is defined as follows. Any minute which contains a deceleration is first discarded. For each valid minute the range is calculated as the maximum positive to maximum negative FHR variation from the baseline FHR. The average range value is calculated for each frame and this provides the MMR. Accelerations are also defined by the user along the top 22b of this table e.g. an increase in FHR by 15 bpm over a 15 second window. These accelerations can be further subdivided into small and large accelerations. The whole file is then analysed by the user in the set frame length and a table is produced of the values of each of these FHR parameters over each frame.

The lower set of tables 23 in FIG. 2 is a different presentation of the upper tables. Again the FHR parameters can be set by the user but as well as a table of the values frame by frame it is also possible to observe a chart (or graph) 21 of these values throughout the recording. The chart shown here illustrates the baseline FHR but equally any other parameter could be plotted, e.g. number of decelerations, accelerations, etc. In addition to these charts, two FHR variability parameters have been introduced, namely SD and RMSSD. The SD is the standard deviation of the FHR compared to the baseline or mean heart rate. The RMSSD in this case is the root mean square of the successive differences of the 2 or 3.75 second average FHR since this file is working on average data and not beat-to-beat data.

The advantage of this form of tabular and chart data presentation is that it allows the clinician to obtain a summary of the user defined FHR parameters (in terms of SW, SD, RMSSD, MMR, accelerations, etc) over the previous longitudinal period (e.g. from 7 hours to 7 days) of monitoring thereby establishing a normality and avoiding the disadvantages of short recordings creating aliasing.

To complement this FHR data, we also present the addition of long term contraction monitoring. This will show the time location of the contraction in relation to the associated FHR data. Hence decelerations in FHR can be related to the presence or non-presence of contractions. This will allow late and early decelerations (see later) to be logged and summarised over a recording session.

There is therefore provided an analysis tool of FHR combined with uterine activity where the user can specify the values of the "FHR watching" parameters (such as STV, SD, RMSSD, MMR, accelerations) and "uterine activity watching" parameters. Exemplary UA parameters could include any of: duration of contraction, time of peak contraction, contraction strength, number of contractions per unit time, early and late deceleration quantification with respect to FHR, etc). This analysis tool can therefore display summarised FHR and UA parameters over the length of the recording in both off-line and real-time modes so as to remove the subjective element of clinical interpretation.

Thus, in a general aspect, the analysis tool collects long-term fetal heart rate data and uterine activity data from sensors disposed on the abdomen of a pregnant mother. The sensors obtain electrical signals indicative of fetal heart rate and uterine activity. The analysis tool includes a means for processing the electrical signals to obtain at least one and preferably more than one fetal heart rate parameter and at least one and preferably more than one uterine activity parameter. The analysis tool includes means for providing as output a graphical or tabular form of the at least one fetal heart rate parameter and said at least one uterine activity parameter for timed frames. The fetal heart rate parameter is preferably selected to include at least one of baseline heart rate, heart rate variability (e.g. STV, SD, RMSSD, MMR), beat-to-beat time interval, RMSSD of beat time intervals, number of heart rate accelerations and number of heart rate decelerations. The FHR parameter may be derived from averaged and/or beat-to-beat data. The uterine activity parameter is preferably selected to include at least one of contraction time location, contraction duration, contraction strength and time occurrence relative to a fetal heart rate deceleration. The analysis tool is preferably adapted to provide the output in respect of timed frames having a duration of at least 30 minutes and a long-term collection and output of said parameters over a period of at least one hour. Preferably, the FHR and UA watching parameters are selectable or specifiable by the user of the analysis tool by means of any appropriate user interface.

The standard NST is carried out using a 2 or 3.75 second FHR moving average because most NST's are based around the use of a Doppler CTG which can only produce an average FHR. This reduction in the apparent variability seen in the FHR trace reduces the sensitivity of the SN technique in detecting fetal stress over a period of 24 hours. A preferred parameter to monitor is the true short term variability (TSTV) measured for example using RMSSD etc. This applies to both fetus and mother.

As a result we present here a modification to the traditional NST referred to as "iNSTant" i.e. integrated NST during the antenatal period. Here we use a pair of electrophysiological electrodes to acquire the following long and short term parameters: FHR; MHR; EHG; extraction of heart rate parameters from averaged FHR, i.e. SN, number of accelerations and decelerations, baseline heart rate etc; extraction of heart rate parameters from true beat-to-beat fetal and maternal heart rate i.e. RMSSD, spectral content, entropy; and fetal ECG morphology and morphological changes.

The ability to continually present all of these parameters in the form of our "iNSTant" NST via passive abdominal cutaneous electrodes offers the clinician tremendous advantages in terms of: reliability of generating data; non-invasiveness of monitoring; patient comfort; ability to perform long term monitoring; ability to continually map fetal well-being; and a reduction in set-up time for a clinician or midwife compared to Doppler CTG.

A half hour frame of data is usually sufficient to illustrate fetal wellbeing. However, over 24 hrs this could be 48 frames. The continuous recording of these frames allows early fetal demise to be detected with greater sensitivity than the traditional under-sampled intermittent Doppler CTG device. By providing both FHR and uterine activity in one device allows decelerations to be classified in terms of late and early decelerations. A late deceleration is one where the FHR decreases after the end of a contraction. On the other hand an early deceleration is one where the nadir of the FHR deceleration occurs at the same time as the peak of the contraction. By monitoring such parameters over long time periods allows the acidosis state of the unborn child to be charted.

FHR values derived from prior art ultrasound techniques are generally based on an average heart rate measured over typically 2 or 3.75 second windows. The apparatus described here can perform beat-to-beat detection of fetal heart time intervals. Two common beat-to-beat parameters that are used in adult ECG are the RMSSD and entropy. RMSSD is the root mean square of the successive difference of a time series of beat-to-beat data. The measure of the RMS over a particular averaging window length allows a time series to be plotted of the true STV. The entropy analysis technique is based around the statistics of the beat-to-beat heart rate data. Entropy is a measure of how unpredictable or surprising a beat is in its time location. If each beat arrived at a set time interval then the entropy would be classified as very low. A healthy heart is one that has relatively high entropy. However, if a long time series is broken up into a series of shorter time series and the entropy is measured for each short series and plotted as a graph of entropy versus time then a multiscale entropy plot is obtained. It is the shape of this plot and that of the RMSSD time series that indicates the health or otherwise of a healthy fetus. The former gives the state of the fetus during the whole recording whilst the RMSSD gives the time varying state of the fetus.

The detection of the FECG morphology provides information about the status of the fetal heart and parameters such as QRS width, PR interval, ST elevation etc can all be measured and logged over a period of time. In addition FECG shape changes are also an indication of fetal movement. The presence of fetal movement is a further indication of fetal well-being that provides reassurance for both the clinician and the mother.

EHG Detection Algorithm

An implementation of the detection of the EHG from a maternal electromyogram signal will now be discussed.

Figure 3:
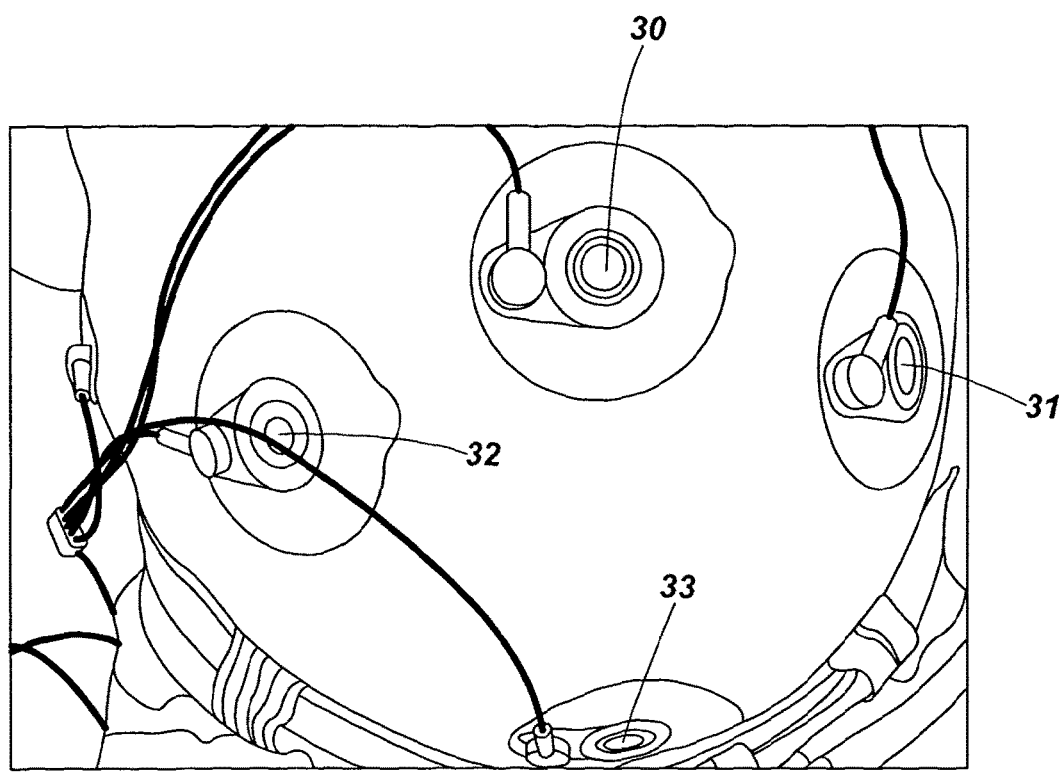
FIG. 3 is a photograph showing electrode positioning on the human maternal abdomen.

With reference to FIG. 3, a signal indicative of uterine activity is obtained from a number of electrodes 30 to 33 placed on the maternal abdominal wall. Preferably, at least two electrodes are used. Preferably, the electrodes are conventional Ag/AgCl ECG electrodes that have a saline gel suspended in foam between the Ag/AgCl and the underlying abdominal skin. A first electrode 33 is placed at the symphis pubis region and a second electrode 30, 31 or 32 can be placed between a line at the level of the navel or umbilicus and the line of the uterus fundus. Alternatively, the second electrode can be placed between a line 5 cm below the uterus fundus and the line of the uterus fundus.

Three 'second' electrodes 30-32 are shown positioned in this case on the uterus fundus in FIG. 3. Any of these three second electrodes can be used to detect the EHG. In a preferred embodiment, the second electrode is on the left lateral side of the mother. All signals measured at each of the three second electrode 30, 31, 32 positions are with respect to the first electrode 33 positioned at the symphis pubis. A further or fifth electrode (not shown) may be used as a right leg driver electrode which actively reduces the noise detected on the patient. Such electrodes are known in the art and may be attached using adhesive, for example. The further electrode achieves noise reduction by feeding a signal back into the patient equal in magnitude to the common mode input noise but 180 degrees out of phase. This significantly attenuates the common mode noise present on the mother's abdomen.

Figure 9:
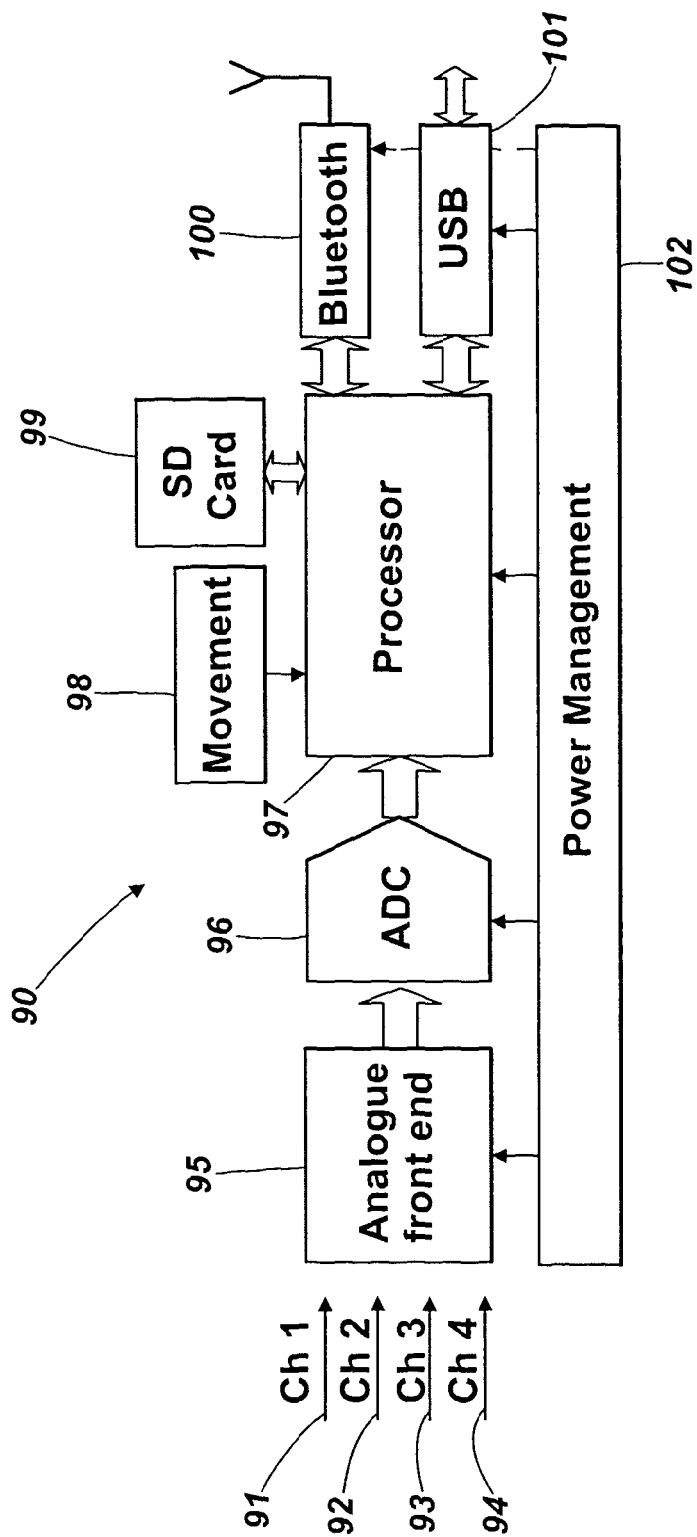
FIG. 9 is a schematic block diagram of hardware suitable for long term monitoring of electrophysiological parameters of a pregnant mother and fetus.

With reference also to FIG. 9, each uterus fundus electrode 30, 31 and 32 paired with the symphis pubis electrode 33 defines one channel 91, 92, 93, 94 and is used to feed an instrumentation amplifier having two inputs. The instrumentation amplifier for each channel forms part of an analogue front end 95 to the uterine activity detector apparatus 90. Each instrumentation amplifier 95 acts as an analogue difference amplifier for removing noise common to both inputs. Combining this with the right leg driver circuit results in a system having a high common mode rejection ratio. This allows differential signals such as fetal ECG, maternal ECG and uterine contractions to be measured. In the case of uterine contractions these pass as a wave down the abdomen. These uterine contractions are manifested as electromyogram signals and in particular are referred to as the electrohysterogram (EHG). As long as the EHG appears at one uterus fundus ('second') electrode 30, 31, 32 but not at the symphis pubis ('first') electrode 33 then a difference signal between the first and second electrodes can be obtained. The first and second electrodes should be separated sufficiently. A minimum separation distance is 5 cm and typically this can be 15 cm. However, too large a separation results in the upper electrode being outside of the uterus and hence unable to detect the contraction. The separation of the uterus fundus from the symphis pubis follows the well documented measurements and is a function of gestation—see "Symphysis fundal height curve—a simple method for foetal growth assessment", Rai et al, Journal of PG medicine, 1995, vol 41, issue 4, pp 93-94.

The lower cut off frequency of the EHG is much lower than that of the FECG and MECG having frequencies as low as 0.1 Hz. As a result the EHG channel should preferably have a wider bandwidth than the normal FHR channel. In a preferred embodiment the analogue EHG detection circuit has a bandwidth of approximately 0.2 Hz to 150 Hz with a gain of approximately 3,000 deployed. The first stage of this analogue detection circuit (instrumentation amplifier in analogue front end 95) has a common mode rejection ratio (CMRR) of better than 120 dB with a power supply rejection ratio above 110 dB.

Figures 4, 5A, 5B, 5C:
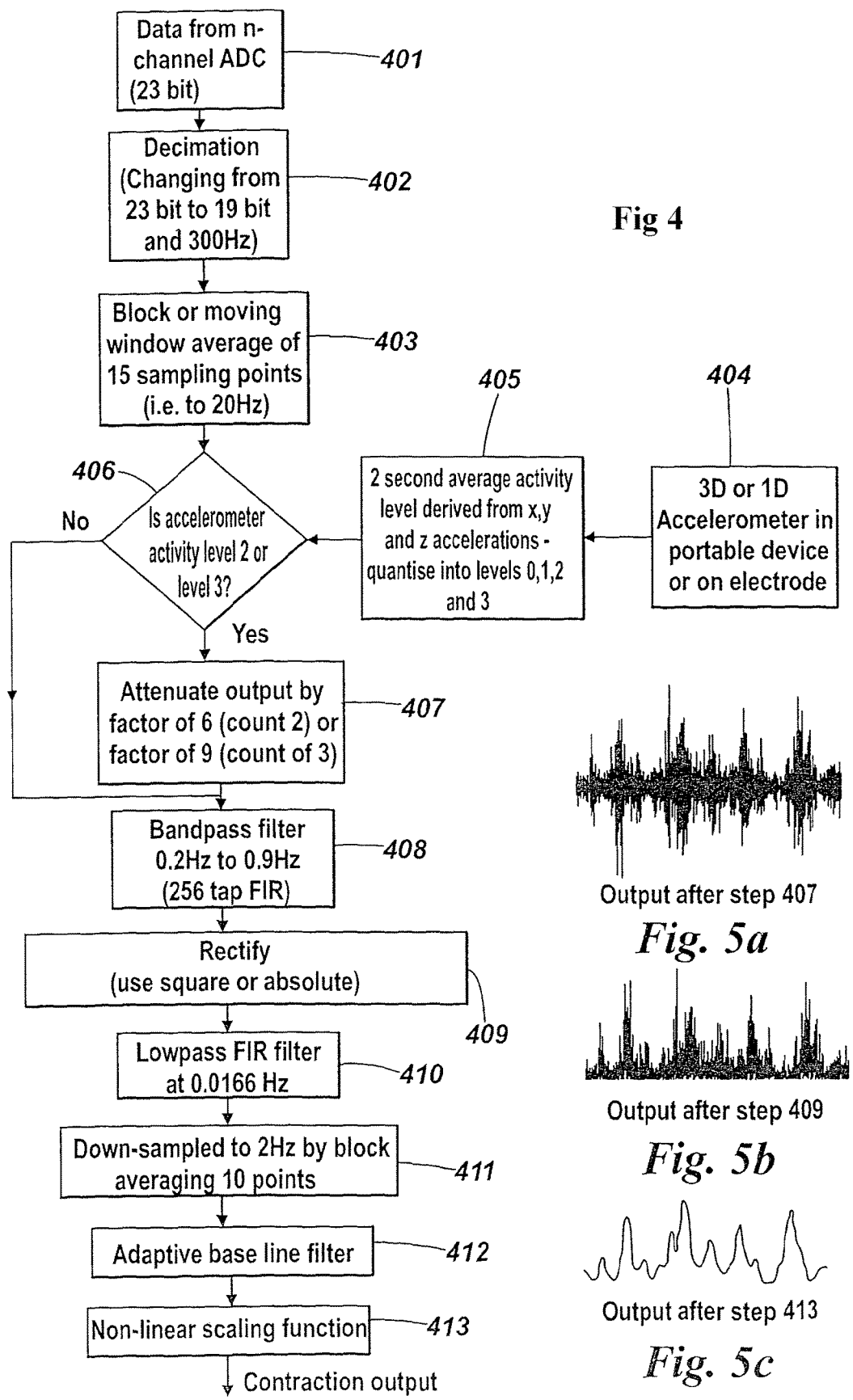
FIG. 4 is a flowchart showing an algorithm for determining a uterine activity signal from electrohysterogram data.
FIGS. 5a, 5b and 5c are plots of uterine activity data as a function of time at various stages of the processing algorithm shown in FIG. 4.

The bandwidth limited amplified analogue signal is then fed into a 23 bit (plus one signed bit) analogue to digital converter (ADC) 96, which samples at typically 900 Hz, where it is digitised and then processed using a digital signal processor 97. The EHG digital processing performed by processor 97 is illustrated in FIG. 4.

A preferred digital processing of the electrophysiological signal in order to produce the electrohysterogram is as follows. Firstly, the data from ADC 96 is input (step 401) is pre-processed by decimating (step 402). This is achieved by discarding 2 out of 3 data points and the resolution is therefore reduced to 19 bits. Alternatively the signal can be sampled at 300 Hz with 19 bit resolution. Other similar frequency and sampling resolution may suffice. The data is then averaged over 15 sampling points to create a new sampled data set at 20 Hz (step 403). In the event of increased high frequency noise then step 403 can be modified by averaging the data over 30 sampling points to create a new sampled data set at 10 Hz. The averaging technique utilised is preferably a moving window average but other averaging methods can be used such as block averaging.

In order to avoid false EHG signals caused by abdominal electromyogram motion artefacts, a movement detector, e.g. sensor 98 (FIG. 9) is used. Preferably, the movement sensor is an accelerometer, although any device capable of providing an indication of physical movement, or acceleration, of the maternal body or abdomen may be used. Preferably, a 3D (or 1D) movement sensor or accelerometer 98 is incorporated into the portable uterine activity detector apparatus 90. Alternatively, the movement sensor or accelerometer 98 may be incorporated into one or more of the abdominal electrodes 30 to 33, or it could be separately attached to the maternal body.

In a preferred embodiment, the movement sensor is a 3D accelerometer having three independent sensors each capable of detecting motion or movement in one of the three Cartesian coordinate axes. Each sensor has a full scale sensitivity of 2 g (where "g" refers to the acceleration determined by earth's gravity). The instantaneous acceleration measure for each of the three axes' sensors is combined to form a combined activity measure, Activity(i), according to the following equation:

$$\text{Activity}(i) = \text{Absolute}(X_t - X_{t-1}) + \text{Absolute}(Y_t - Y_{t-1}) + \text{Absolute}(Z_t - Z_{t-1})$$

where $X_t$, $Y_t$, $Z_t$ are the instantaneous accelerations at time point t while $X_{t-1}$, $Y_{t-1}$ and $Z_{t-1}$ are the instantaneous accelerations for the previous sample time point t−1. Subtracting the current accelerometer values from the previous values provides a high pass filter which removes acceleration due to gravity and flicker (1/frequency) noise.

The average overall activity over a 2 second window is calculated as the sum over l=1 to N of all Activity(i) values, i.e.

$$\text{Average Activity}(N) = \frac{\sum_{i=1}^{N} \text{Activity}(i)}{N}$$

where the integration window N is preferably 80 samples for a 40 Hz sampled accelerometer output in order to obtain a preferred 2 second average. Other averaging windows can be taken such as values of N=40, 160, 400, 600 etc. However using too large a value of N may distort the measured contraction and can on occasions suppress a contraction. Either a block window or a moving window averaging process can be used. Although it is possible to use the sum of the squared differences viz:

$$\text{Activity}(i)' = [(X_t - X_{t-1})^2 + (Y_t - Y_{t-1})^2 + (Z_t - Z_{t-1})^2]^{0.5}$$

this squaring action places a heavier demand on processor resources and hence the absolute process is the preferred option. The value of the "Average Activity(N)" is represented as an 11 bit binary number such that full scale represents an acceleration of 2 g. The "Average Activity(i)" values are then divided into four non-equal ranges. For example if the number of bits is 6 or less (i.e. $6 \times 2/2^{11}$ g which is approximately 6 mg) then this is classified as "ACTIVITY LEVEL 0". If the number of bits is between 7 and 50 (i.e. 7 mg-50 mg) then this is classified as "ACTIVITY LEVEL 1". When the number of bits lies between 51 and 200 (i.e. 51 mg-200 mg) then this is classified as "ACTIVITY LEVEL 2". Finally, if the number of bits is greater than 201 (i.e. >201 mg) then this is classified as "ACTIVITY LEVEL 3".

In the case of a 1D accelerometer the single axis output may be used to determine an AVERAGE ACTIVITY value by again using the absolute difference between the current accelerometer sample and the previous sample point.

With further reference to FIG. 4, when large activity is detected, e.g. ACTIVITY LEVELS 2 and 3 (step 406), the signal is attenuated (step 407) by either a factor of six (for ACTIVITY LEVEL 2) or by a factor of nine (for ACTIVITY LEVEL 3). An illustrative output after step 7 is given in FIG. 5a. The accelerometer or movement sensor 98 offers a substantial improvement in the accurate and reliable determination of the frequency and duration of contractions. The activity monitoring provided by the movement sensor allows suppression of false positive contractions when the mother is active. Thus, in a general aspect, the signal processor 97 separates a uterine electromyogram signal from fetal and maternal heart rate signals and then filters or attenuates motion artefacts from the uterine electromyogram signal using the movement signals from a movement sensor 98 or other movement detector to generate electrohysterogram (EHG) data from the uterine electromyogram signal. Preferably, the filtering or attenuation of motion artefacts from the electromyogram signal is performed as a function of the magnitude of the movement signals, and more preferably as a non-linear function of the magnitude of the movement signals. It can be considered that true electrohysterogram data is derived from the uterine electrohysterogram data by the removal of artefacts such as maternal and/or fetal motion artefacts.

When the electromyogram signal is attenuated as a function of the movement signals, a low confidence level may also be indicated to the user on an output display, e.g. by providing a grey background on the display over the EHG trace when the ACTIVITY LEVEL is >1 for typically more than 1 minute. Hence even if false positives do occur the user (who could be positioned remotely some distance from the mother, i.e. at the hospital), is aware that the data is of low confidence.

The signal is then band-pass filtered (step 408), e.g. using a 256 tap FIR filter, between 0.2 Hz and 0.9 Hz. In order to obtain the envelope of this signal the band pass filtered data is usually first rectified by squaring (step 409). An illustrative output after step 409 is given in FIG. 5b. However, squaring can create overflow and hence the data may be adjusted such that all negative values are converted into positive values. For example, a modulus or absolute may be taken (step 409). In a preferred arrangement, although not shown in FIG. 4, prior to rectifying the data by squaring, taking a modulus or absolute (step 409), fetal motion artefacts are removed. Fetal motion artefacts can couple in the bandwidth 0.2 Hz to 0.9 Hz. However, the length of one fetal motion artefact is narrow and its amplitude is high. Fetal motion artefacts can be removed by discarding, in every 30 second window, positive signals that have a value N times higher than the mean of the positive values in the 30 second window and/or discarding, in every 30 second window, negative signals that have a value N times lower than the mean of the negative values in the 30 second window. The value of N can be determined empirically and is preferably in the range of 2 to 3. Alternatively, the fetal motion artefacts may be removed by a clipping algorithm that removes 20% of each 30 second block that corresponds to the largest positive and negative amplitudes. In a general aspect, fetal motion artefacts may be removed by any suitable clipping algorithm that selectively removes peak excursions in the data, in a positive and negative direction, based on an average value of the data, selected over a predetermined time window. In one aspect, it is possible to remove fetal motion artefacts from the electrohysterogram data without removal of the maternal motion artefacts using the processes defined above.

In order to produce an envelope of the ENG signal, the rectified data is further filtered by a low-pass filter (step 410) having a cut-off no greater than 0.0166 Hz (i.e. a time constant of greater than 60 seconds) to obtain the envelope of the EHG signal.

The steps 409 and 410 implement a rectification and low pass filter to generate an enveloped trace. Several forms of rectification and low pass filter actions can be implemented. An alternative to the one described in the above paragraph is to compute a 30 second wide moving RMS value for the output of step 408. The RMS is computed from the data after fetal motion artefact removal (the clipped data). This clipped data, having passed through a "root mean square process" can be further low pass filtered by calculating an "integral of the absolute value of the waveform" or passing to a low pass filter having a cut off no greater than 0.0166 Hz (step 410) which generates the output after step 410.

The envelope may then be down-sampled (step 411), e.g. to 2 Hz by block averaging 10 points. A moving window average is preferred but other averaging techniques may be used such as a block window average. In order to avoid baseline wander (i.e. below 0.0166 Hz), an adaptive base line filter may be deployed (step 412). The baseline is computed for each point by finding the minimum of the previous "x" seconds (where "x" could be for example 30 seconds up to 4 minutes). This minimum is fed to an exponential low pass filter to produce the baseline value that is then subtracted from the original data. This process is repeated in real time throughout the record. Such a process allows the removal of baseline wander that occurs in such EHG data. Thus, in a general aspect, baseline wander may be removed by the process of, for every specific data point, determining a minimum value from a set of preceding data points to act as a "baseline value" and subtracting that baseline value from the specific data point. Preferably, the set of preceding data points used comprises those in a window of 'x' seconds prior to the specific data point, as discussed above. It will be understood that variations may be made to the process. For example, the baseline value may be determined for and applied to groups of specific data points. In alternative processes, the baseline wander could be removed by periodically determining a baseline value from a minimum value of the electromyogram data in a first period and subtracting that baseline value from the electromyogram data in that first period and/or a succeeding period following the first period.

The data is finally scaled or normalised with a non-linear function (step 413). An illustrative output after step 413 is given in FIG. 5c. In preferred embodiments, the non-linear function is one or more of a quarter cycle sinusoid (between zero and pi/2 radians), sigmoid, compounding or logarithmic function, for example. Preferably, the non-linear function ensures that the data set fit into a 0 to 255 range. In order to reduce the processing load, a look up table is preferably used. The range value is optional and is preferably chosen to comply with the standard "CTG series 50 protocol" using "Toco coding" reserved word that is found on most commercial CTG machines in obstetric use today. The addition of this non-linear step is preferable for maintaining a good correlation with the IUPC gold standard particularly in terms of the contraction frequency, contraction duration and contraction strength. Thus, in a general aspect, the signal processing scales the EHG data with a non-linear function to provide a measure of contraction strength. Preferably, the scaling function is particularly adapted to ensure that the EHG data correlates with intrauterine pressure catheter measurements. The magnitude of the EHG signal greatly depends upon the electrode separation and location on the mother's abdomen. One setting of electrode separation/location has been specified in UK patent applications 0810843.3 and 0819887.1. In order to calibrate the EHG signal with intrauterine contraction strength, a statistical proportion of mothers (approximately >25) are recorded through labour and delivery. The axis is scaled such that the maximum EHG detected corresponds to 100-120 mmHg of intrauterine pressure. Hence whatever electrode configuration is used then as long as a statistical number of mothers are recorded during labour and delivery then that electrode configuration can be calibrated for intrauterine pressure. Thus, in a general aspect, the scaling of the EHG signal in terms of intrauterine pressure may be effected by a statistical sample of mothers during labour.

This technique allows the contraction frequency, duration and strength to be monitored in a simple pair of electrodes, e.g. second electrode 33 in conjunction with any one of first electrodes 30 to 32. As a result it provides a highly attractive alternative to the invasive "intrauterine pressure catheter" and the less reliable Toco in use today.

The EHG routine in FIG. 4 may then store the uterine activity data (e.g. in a storage device 99 or transfer it via a suitable communication channel 100, 101 (FIG. 9), such as Bluetooth or USB. The under-sampled non-linear data may be transferred together with FHR data (e.g. average and beat-to-beat), MHR data (average and beat-to-beat) and maternal activity data, for display or storage.

Figure 8:
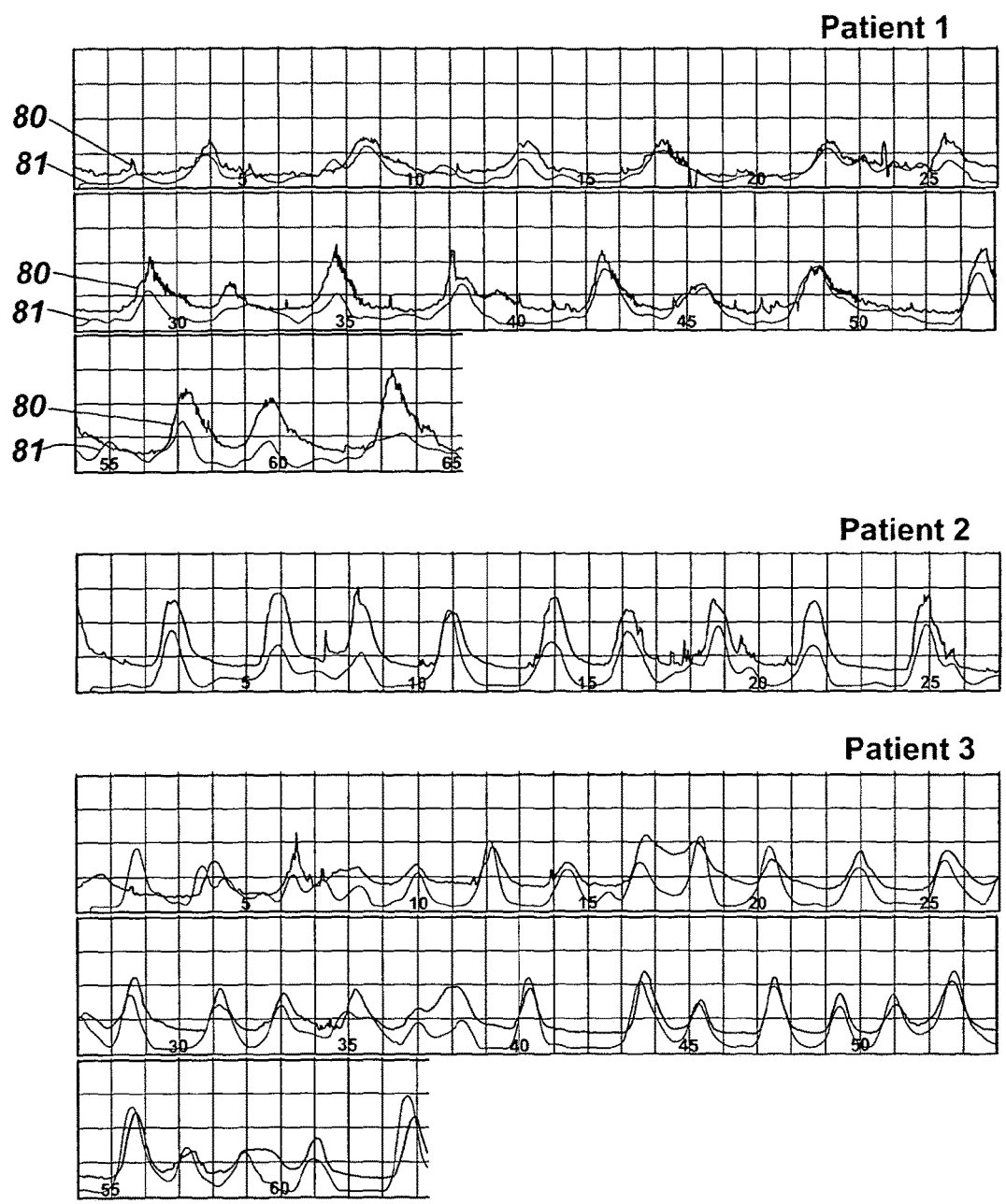
FIG. 8 is a series of graphs representing contraction signals as measured using an intrauterine pressure catheter compared with contraction signals determined from EHG data.

This EHG algorithm was validated on 40 patients during labour who had both the EHG electrodes applied along with an intra uterine pressure catheter (IUPC) inserted into the cervix for comparison. The EHG algorithm detected 94.6% of the 800 contractions detected by the IUPC with a positive predictive value of 85.6%. Three examples from three different patients of the IUPC comparison against EHG are shown in FIG. 8 which shows excellent correlation with the IUPC contraction strength, duration and frequency. In FIG. 8, the trace 80 represents a pressure measurement of uterine activity as a function of time, as recorded by the IUPC, and the trace 81 represents the computed electrohysterogram output from the algorithm of FIG. 4 as a function of time using filtering based on a movement sensor.

It should be noted that any other maternal activity or movement indicator could be used in place of the 1d or 3d accelerometers described, to provide assistance with eliminating false positives. Various activity instruments, sensors, or transducers are possible, such as a gyro, an inertial motion sensor; mercury switches, smart materials on the abdomen (i.e. those whose resistance for example changes with movement), etc. An additional method to detect maternal movements that does not require any additional sensor or transducer is to use the magnitude of maternal ECG detected by the electrodes itself as a movement sensor. The magnitude of adult electrocardiogram QRS signals varies with the breathing rate of the adult. When electrodes are placed on the abdomen of a mother, not only does the ECG height vary with respiration but it also varies with maternal movement. Filtering out the effect of breathing on the maternal ECG leaves behind ECG QRS height changes as a function of maternal movement. This feature is highly useful and can be deployed as a maternal movement indicator for not only removal of false positive contractions but also as a generic movement indicator. Thus, the movement signals indicative of a movement of the maternal body required for the filtering of motion artefacts may themselves by obtained from the cutaneous electrodes and extracted from the maternal ECG data. Thus, in a general aspect, the movement signals may be derived from an amplitude of maternal ECG as a function of time and the signal processing means may be adapted to measure maternal ECG as a function of time and determine movement of the maternal body therefrom.

Figure 6:
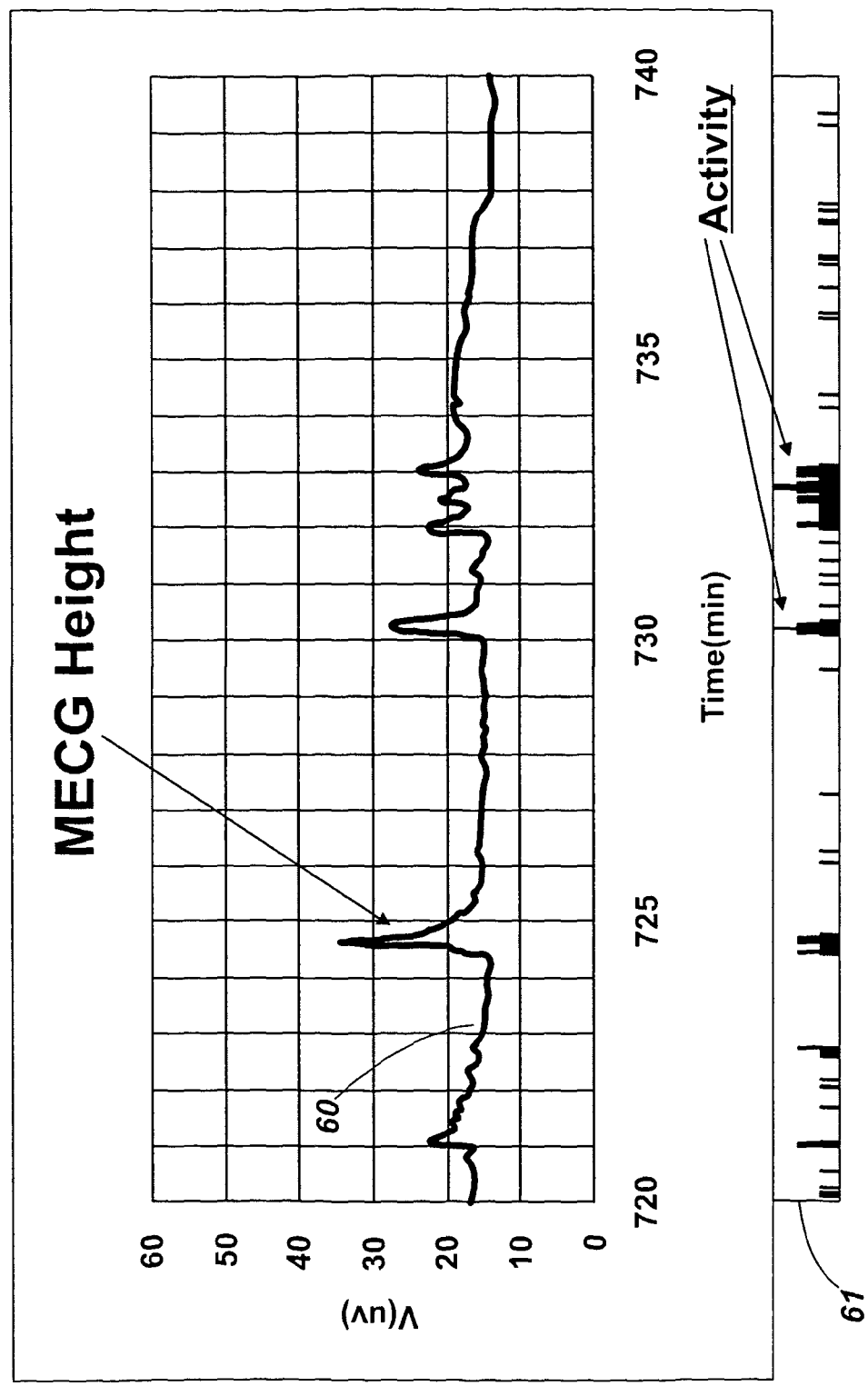
FIG. 6 is a plot of maternal ECG QRS height as a function of time, taken from the abdomen and compared with an accelerometer sensor signal.
Figure 7:
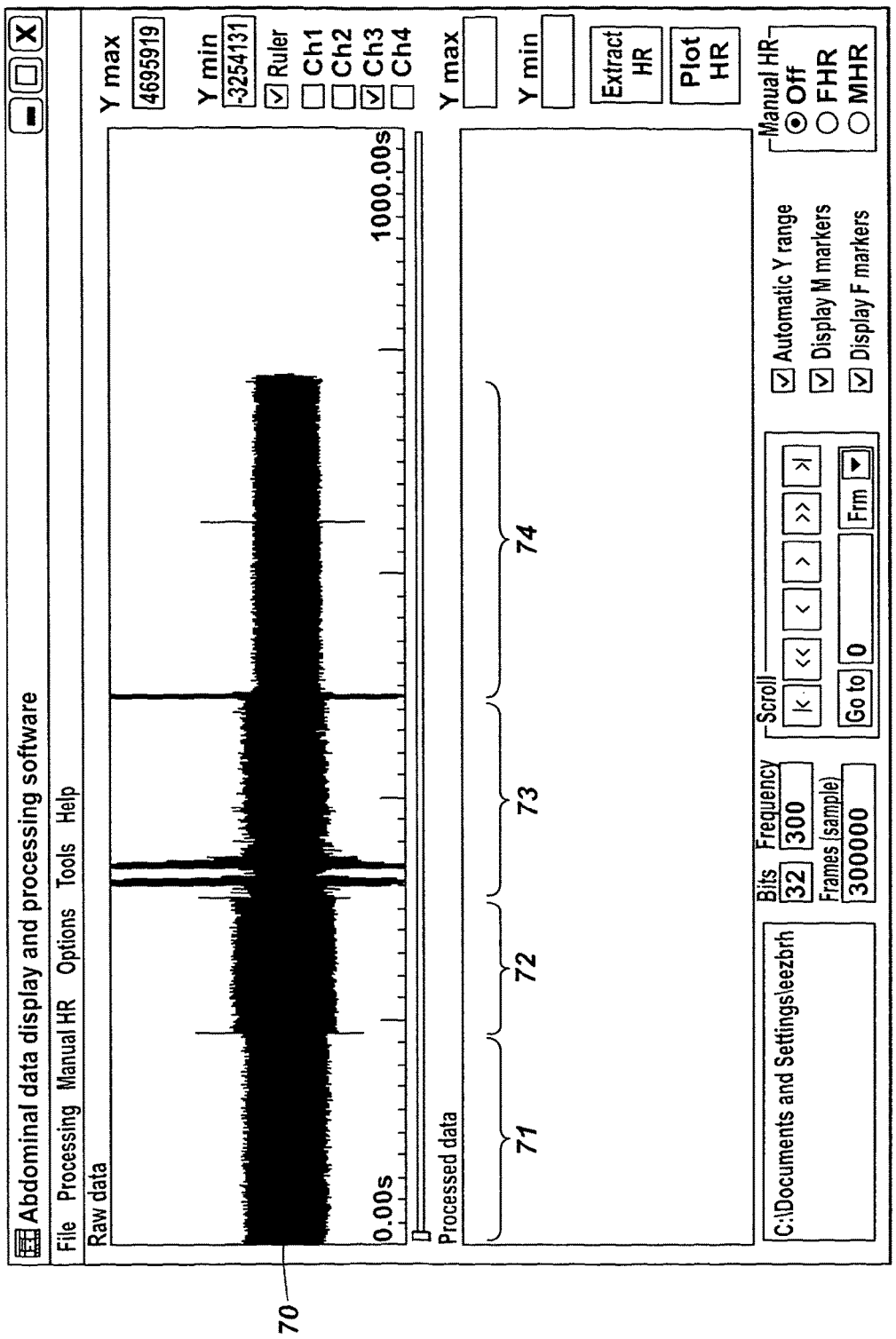
FIG. 7 is a plot of maternal ECG QRS height as a function of time, taken from the abdomen while the maternal body is in four different positions.

FIG. 6 shows a trace 60 of maternal ECG QRS height as a function of time recorded from electrodes on the abdomen at the same time as the average activity level. The activity level trace 61 represents activity determined by an accelerometer. We can see that when a movement is detected then the ECG amplitude changes. FIG. 7 also shows an ECG QRS height (trace 70) as a function of time recorded from electrodes on the abdomen as the patient changes position.

The trace 70 is divided into four regions, 71, 72, 73, 74. Region 71 corresponds to a sitting back position; region 72 corresponds to a sitting forward position; region 73 corresponds to a sitting with legs flat position; and region 74 corresponds to a lying down position.

UA and FHR are two key parameters indicating fetal wellbeing commercially recorded during pregnancy. However, these commercially available cardiotocograph monitors utilise two separate transducers. By using skin electrodes both of these parameters can be detected with the same single transducer (i.e. skin electrode) thereby greatly simplifying the apparatus and method. A single pair of electrodes allows the monitoring of fetal and maternal beat-to-beat information and fetal ECG morphology. Adding an accelerometer to the instrument and/or electrode allows maternal activity to be monitored and greatly assists during the automatic extraction of uterine activity, fetal and maternal heart rate and FECG morphology. In particular as we have seen false positives on contraction presence can be eliminated using the activity level of an accelerometer.

Monitoring During Labour and Preterm Labour

Usage of the electrophysiological uterine activity detector apparatus 90 during labour and preterm labour will now be described.

Preterm labour is defined as the period when an expectant mother enters labour before the expected term date. Fundamentally very early arrival of labour poses a threat to the unborn fetus. These threats are for example the insufficient development of the fetus's vital organs such as the lungs. The longer the fetus remains in the uterus the better the chance of a reduction in morbidity and hence a reduction in any long term illnesses. Tocolytic therapy is applied to slow down the onset of labour. This can be considered as a potentially dangerous situation for both fetus and mother. Recording both the EHG and the FHR will greatly assist the clinician to asses whether labour is being slowed and whether the fetus is in a well state. Monitoring the fetal (and maternal) beat-to-beat information via RMSSD, spectral response, entropy etc provides an early warning ahead of the STV derived from the 2 second (or 3.75 second) average heart rate. Being able to count the number of contractions, their duration and their strength from the EHG using the same electrodes as the fetal ECG allows progress of labour to be readily monitored. The apparatus, being small and portable, lends itself to long term monitoring which is difficult with the Doppler ultrasound CTG instruments. Such a situation of slowing down the onset of labour can often occur for several days and the ability to continuously and non-invasively monitor the fetal heart rate, contractions and fetal beat-to-beat data over this length of time is invaluable for the wellbeing of the fetus and the mother.

During spontaneous labour, for a term mother, a similar situation occurs. However, here the progress of labour is required to proceed at a steady rate. The measurement of the progress of labour is carried out by measuring the cervical length with transvaginal ultrasound, or the traditional digital vaginal examination. By using the contraction count, duration and strength in an ambulatory setting the progress in early labour can be monitored.

Electronic Hardware Apparatus

The electronic hardware that is required to detect long term electrophysiological signals from the fetus and mother is shown as a schematic block diagram in FIG. 9. Each channel 91-94 (defined as one uterus fundus electrode 30, 31 or 32 with respect to the symphis pubis electrode 33) uses an instrumentation amplifier having two inputs. One input is connected to the symphis pubis electrode ('first' electrode) whilst the other input is connected to one of the three 'second' electrodes which may lie on the line parallel with the uterus fundus or on a horizontal line passing through the umbilicus of the mother. The analogue front end 95 is an instrumentation amplifier which acts as an analogue difference amplifier removing noise common to both inputs. Combining this with the right leg driver circuit (not shown in FIG. 9) results in a system having a high common mode rejection ratio. Four channels are indicated here. The fourth channel consists of a wider bandwidth channel for the detection of EHG. The output of the analogue front end feeds into an ADC 96 having a resolution of 23 bits plus 1 signed bit and the digitised output data is fed into the real-time processor 97. In parallel with this the movement data is interlaced so as to allow discrimination of motion artefacts from the processed signals (UA, FHR, MHR etc). Data is stored locally on a memory card 99 and is sent if required via a wireless link 100 such as Bluetooth or any other wireless technology. A USB option 101 is available for downloading the data stored on the SD card 99. An overarching power management system 102 monitors power levels and places individual blocks into low power sleep mode when not in use. The overall system currently fits into a mobile phone size case. However, such a system can be implemented onto a hybrid substrate mounted onto the electrodes 30-33 or a single piece of silicon in the form of a custom integrated circuit.

If a movement sensor is to be incorporated into one of the electrode, an integrated electrode and movement sensor for attachment to the maternal abdomen is provided for generating electromyogram signals from the maternal body and movement signals indicative of a movement of the maternal body. The integrated electrode comprises an electrical contact portion for establishing electrical contact with the skin of the abdomen in known manner, an attachment means for securing the integrated electrode and movement sensor to the body, e.g. using an adhesive portion in known manner; and a transducer or sensor adapted to generate movement signals indicative of movement of the maternal body.

Other embodiments are intentionally within the scope of the accompanying claims.

The invention claimed is:

1. Apparatus for detecting uterine activity comprising:
a plurality of cutaneous electrodes, the cutaneous electrodes configured for attachment to a maternal abdominal wall:
a first input configured to receive electrical signals from the cutaneous electrodes;
a movement sensor configured to provide movement signals indicative of a physical acceleration of a maternal body or abdomen;
a second input configured to receive the movement signals from the movement sensor;
an output;
a signal processor coupled to the first and second inputs and the output, the signal processor configured to separate a uterine electromyogram signal from fetal and maternal heart rate signals in the electrical signals received at the first input and to filter maternal motion artefacts from the uterine electromyogram signal using the movement signals received at the second input by attenuating the uterine electromyogram signal as a function of a magnitude of the movement signals, the signal processor being further configured to filter fetal motion artefacts from the uterine electromyogram signal by removal of peak excursions in the uterine electromyogram signal based on an average value of the uterine electromyogram signal; and the output configured to present electrohysterogram (EHG) data from the filtered uterine electromyogram signal.

2. The apparatus of claim 1 wherein the signal processor is configured to attenuate or filter the uterine electromyogram signal as a non-linear function of the magnitude of the movement signals.

3. The apparatus of claim 1 in which the signal processor includes an EHG detection circuit with a bandwidth between approximately 0.2 Hz and 150 Hz.

4. The apparatus of claim 1 in which the signal processor includes a bandpass filter between 0.2 Hz and 0.9 Hz.

5. The apparatus of claim 1 in which the signal processor is configured to remove baseline wander from the electrohysterogram data, by determining for every specific data point a minimum value from a set of preceding data points to act as a baseline value and subtracting that baseline value from the specific data point.

6. The apparatus of claim 1 in which the signal processor is further configured to scale the EHG data with a non-linear function to provide a measure of contraction strength.

7. The apparatus of claim 6 in which the non-linear function is configured to return the EHG data that correlates with an intrauterine pressure, wherein the intrauterine pressure is measured using an intrauterine pressure catheter.

8. The apparatus of claim 1 in which at least one of the cutaneous electrodes incorporates a movement sensor.

9. The apparatus of claim 8 in which the movement sensor detects movement or acceleration in three dimensions.

10. The apparatus of claim 1 in which the movement signals are derived from an amplitude of maternal ECG as a function of time, the signal processor being configured to measure maternal ECG and determine movement of the maternal body therefrom.

11. The apparatus for detecting uterine activity of claim 1, wherein the signal processor is configured to filter the fetal motion artefacts from the uterine electromyogram signal.

12. The apparatus of claim 1, wherein the movement sensor comprises an accelerometer or gyro or inertial motion sensor.

13. A method of detecting uterine activity comprising the steps of: generating electrical signals using cutaneous electrodes disposed on a maternal abdomen; obtaining movement signals using a movement sensor to provide movement signals indicative of a physical acceleration of a maternal body or abdomen;
separating, using a signal processor, a uterine electromyogram signal from fetal and maternal heart rate signals in said generated electrical signals and filtering, using the signal processor, maternal motion artefacts from the uterine electromyogram signal using the movement signals by attenuating the uterine electromyogram signal as a function of a magnitude of the movement signals;

filtering, using the signal processor, fetal motion artefacts from the uterine electromyogram signal by removal of peak excursions in the uterine electromyogram signal based on an average value of the uterine electromyogram signal: and providing, using the signal processor, electrohysterogram (EHG) data from the filtered uterine electromyogram signal.

14. The method of claim 13 further including the steps of:
attaching a first electrode to a symphis pubis region of the maternal abdomen; attaching a second electrode to the maternal abdomen, between a line 5 cm below a uterus fundus and a line of the uterus fundus or between a line at a level of a navel or umbilicus and the line of the uterus fundus; generating, by the signal processor, said electrical signals from said first and second electrodes.

15. The method of claim 13 further including the step of obtaining said movement signals from a movement transducer or sensor.

16. The method of claim 13 further including the step of obtaining said movement signals from said electrical signals generated by the cutaneous electrodes.

17. Apparatus for collecting fetal heart rate data and uterine activity data, comprising:
a plurality of cutaneous electrodes arranged to be located on an abdomen of a pregnant mother in use;
signal inputs configured to receive electrical signals-from said electrodes in use, the electrical signals comprising electrophysiological signals indicative of fetal heart rate and uterine activity;
a signal processor configured to process said received electrical signals to generate separate data signals of the fetal heart rate and uterine activity;
the signal processor arranged to extract at least one fetal heart rate parameter and at least one uterine activity parameter from said data signals; and
an output coupled to the signal processor, the apparatus configured to provide to said output a graphical or tabular form of said at least one fetal heart rate parameter and said at least one uterine activity parameter for timed frames;

wherein the signal processor is further configured to obtain a measure of root mean square of successive differences in time series of beat-to-beat time intervals and the apparatus is configured to provide to said output the measure in a graphical or tabular form.

18. The apparatus of claim 17 in which: the fetal heart rate parameter is selected to include at least one of baseline heart rate, number of heart rate accelerations and number of heart rate decelerations; and the uterine activity parameter is selected to include at least one of contraction time location, contraction duration, contraction strength and time occurrence from a fetal heart rate deceleration.

19. The apparatus of claim 17 configured to provide at said output timed frames having a duration of at least 30 minutes and long-term collection and output of said parameters over a period of at least one hour.

20. The apparatus of claim 17, wherein the apparatus is configured to provide said measure of root mean square of successive differences in a graphical or tabular form for timed frames to provide an indication of a correlation between time occurrence of the measure of root mean square of successive differences and a uterine contraction.

21. The apparatus of claim 17, wherein the signal processor configured to obtain a maternal heart rate parameter from the electrical signals from the cutaneous electrodes and the output in graphical or tabular form comprises the maternal heart rate parameter.

22. The apparatus of claim 21 wherein the signal processor is further configured to obtain a measure for the maternal heart rate of root mean square of successive differences in time series of beat-to-beat intervals.

23. The apparatus of claim 17, wherein the signal processor separate the at least one fetal heart rate parameter and at least one uterine activity parameter from common the electric signals from the cutaneous electrodes.

24. The apparatus of claim 17, wherein the signal processor is further configured to obtain time averaged fetal heart rate parameter data and the output in graphical or tabular form further comprises said time averaged fetal heart rate parameter data.

25. The apparatus of claim 17, wherein the cutaneous electrodes include a movement sensor and the signal processor is arranged to filter maternal motion artefacts from said electrical signals.

* * * * *